US012085509B2

(12) United States Patent
Lee

(10) Patent No.: US 12,085,509 B2
(45) Date of Patent: Sep. 10, 2024

(54) SUBMERGED FLUOROMETER WITH LOW EXCITATION ANGLE

(71) Applicant: AquaRealTime, Inc., Boulder, CO (US)

(72) Inventor: Christopher Lee, Boulder, CO (US)

( * ) Notice: Subject to any disclaimer, the term of this patent is extended or adjusted under 35 U.S.C. 154(b) by 0 days.

(21) Appl. No.: 17/793,957

(22) PCT Filed: Jan. 22, 2021

(86) PCT No.: PCT/US2021/014756
§ 371 (c)(1),
(2) Date: Jul. 20, 2022

(87) PCT Pub. No.: WO2021/150991
PCT Pub. Date: Jul. 29, 2021

(65) Prior Publication Data
US 2023/0047096 A1    Feb. 16, 2023

Related U.S. Application Data

(60) Provisional application No. 62/964,149, filed on Jan. 22, 2020.

(51) Int. Cl.
*G01N 21/64* (2006.01)
(52) U.S. Cl.
CPC ... *G01N 21/645* (2013.01); *G01N 2201/0634* (2013.01)
(58) Field of Classification Search
None
See application file for complete search history.

(56) References Cited

U.S. PATENT DOCUMENTS

| 5,461,236 | A  | * | 10/1995 | Gram | G01V 8/10 |
| | | | | | 250/301 |
| 7,209,223 | B1 | * | 4/2007 | Hull | G01N 21/645 |
| | | | | | 356/73 |
| 11,618,870 | B2 | * | 4/2023 | Angelescu | C12M 33/06 |
| | | | | | 73/864.35 |
| 2005/0084419 | A1 | | 4/2005 | Hill et al. | |

(Continued)

OTHER PUBLICATIONS

USPTO, International Search Report, PCT/US2021/014756, May 4, 2021.
USPTO, Written Opinion, PCT/US2021/014756, May 4, 2021.

*Primary Examiner* — David P Porta
*Assistant Examiner* — Djura Malevic

(57) ABSTRACT

The disclosure describes systems, methods, and apparatuses for monitoring fluorescent peaks using a fluorometer, where the fluorometer comprises an instrument assembly, a circuit assembly, a casing, and a window set into the casing, wherein at least a portion of the instrument assembly is submerged within a liquid and above an analyte workspace; a buoy assembly; one or more emission sources electrically coupled to the circuit assembly, the emission sources configured to emit light in one or more frequencies or wavelength bands; a prism arranged in contact with the window, the prism configured to direct emissions from the emission sources towards the analyte workspace, the prism including at least one angled surface; at least one photosensor positioned above the window and configured to detect fluorescence emissions of analytes in the analyte workspace; and a filter array positioned between the window and the photosensor.

8 Claims, 34 Drawing Sheets

(56) References Cited

U.S. PATENT DOCUMENTS

| | | | |
|---|---|---|---|
| 2007/0103681 A1* | 5/2007 | Hull | G01N 21/645 |
| | | | 356/318 |
| 2011/0284769 A1 | 11/2011 | Matsui et al. | |
| 2013/0162999 A1* | 6/2013 | Myrick | G01N 21/31 |
| | | | 356/402 |
| 2013/0327961 A1* | 12/2013 | Tedetti | G01N 33/1886 |
| | | | 250/206 |
| 2014/0103224 A1* | 4/2014 | Ng | G01N 21/255 |
| | | | 250/435 |
| 2015/0000384 A1* | 1/2015 | Chekalyuk | G01J 3/0216 |
| | | | 73/61.48 |
| 2017/0038301 A1 | 2/2017 | Flanagan et al. | |
| 2017/0274378 A1* | 9/2017 | Turner | B01L 3/502715 |
| 2018/0251713 A1* | 9/2018 | Angelescu | C12M 1/34 |
| 2020/0030515 A1* | 1/2020 | Merchant | G01N 21/31 |
| 2023/0047096 A1* | 2/2023 | Lee | G01N 21/6486 |

* cited by examiner

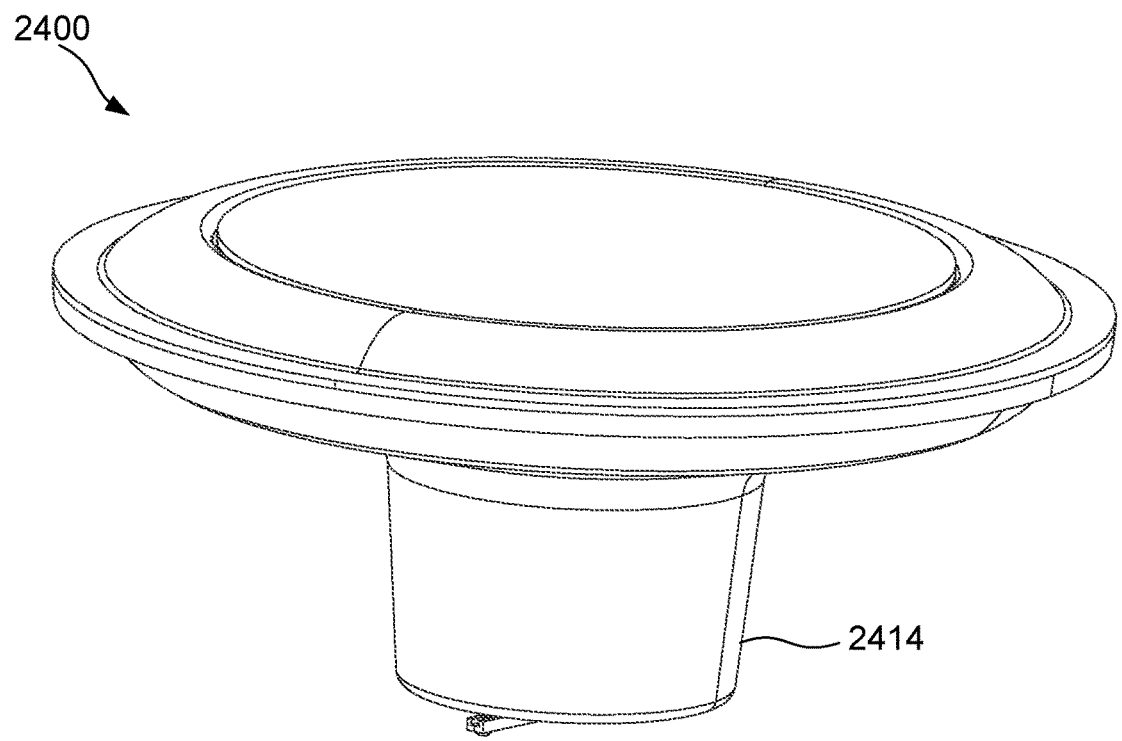
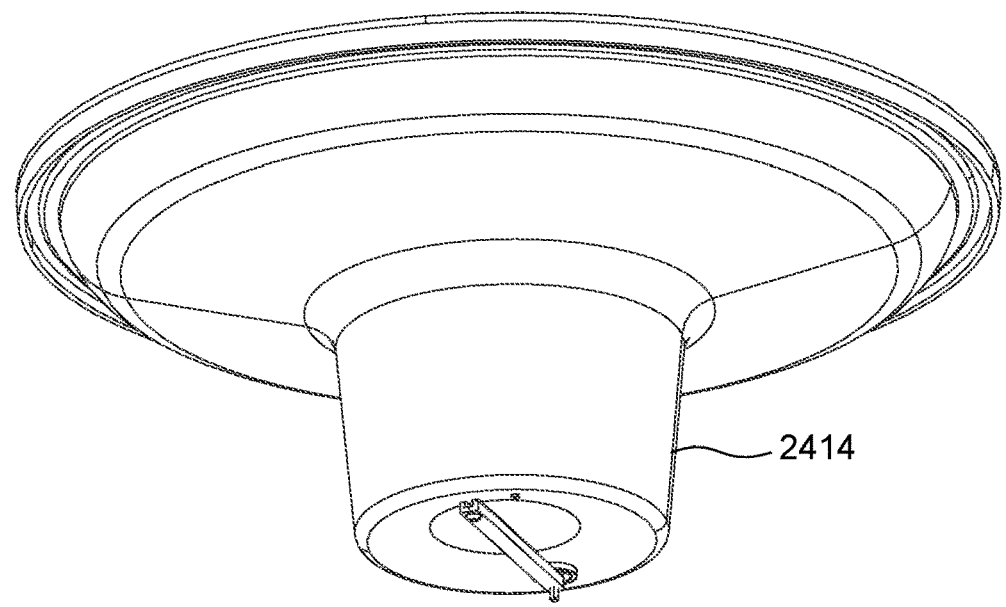
FIG. 24

SUBMERGED FLUOROMETER WITH LOW EXCITATION ANGLE

CLAIM OF PRIORITY UNDER 35 U.S.C. § 119

The present Application for Patent claims priority to U.S. Provisional Application No. 62/964,149 entitled "SUBMERGED FLUOROMETER WITH LOW EXCITATION ANGLE" filed Jan. 22, 2020 and assigned to the assignee hereof and hereby expressly incorporated by reference herein.

FIELD OF THE DISCLOSURE

The present disclosure relates generally to fluorometers. In particular, but not by way of limitation, the present disclosure relates to systems, methods and apparatuses for enhancing the amount of detected fluorescence in a submersible fluorometer.

DESCRIPTION OF RELATED ART

Harmful algal blooms (HABs) exert strongly negative impacts on coastal oceans, lakes, rivers, and municipal drinking supplies world-wide. These can be seen, for example, either directly though production and release of potent neurotoxins and/or through massive die-offs that induce anoxic conditions and extensive fish-kills. Contamination of shellfish with toxins produced by HABs continues to be an ongoing concern for the fisheries, aquaculture industry, and research fields as the HABs cause ocean closures, sale bans, and consumption restrictions. Not only are HABs harmful for human consumers, but the toxic blooms are often devastating to the ecosystem and to a large variety of marine organisms.

SUMMARY

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

Most HAB monitors use the fluorescent characteristics of components in a liquid to identify those components. For instance, upwelling radiation from algae in sea water is a function of chlorophyll concentration and photosynthetic activity, which is measured via the magnitude of the fluorescence peak, as described in A. A. Gitelson, et al., "Remote Estimation of Chlorophyll Concentration in Productive Waters: Principals, Algorithm Development and Validation," Proc. of NWQMC, 149 (2000).

Devices for monitoring fluorescent peaks for HAB as well as other harmful substances in water bodies, tend to either be hand-held, lab-based, or buoy-based. While lab-based systems can be most effective at identification, the challenge of continuously providing water samples to a remote lab limits their effectiveness for continuous water monitoring. Hand-held systems are overly-labor dependent, do not allow 24-7 monitoring, and are more difficult to use more than a few feet from shore. Buoy-based systems overcome the challenges of lab-based and hand-held systems but tend to include sensors that probe more than thirty inches below the surface, despite the majority of plankton activity occurring within twelve inches of the surface. Additionally, most sensing systems use a transparent window to separate electrical components from water, and this window greatly reduces light transmission because of total internal reflection (TIR), unless emissions are made relatively close to perpendicular to the window. However, this need to avoid TIR leads to fluorescent stimulation far below the window surface (e.g., emissions intersecting a normal to the window at a center of the sensor at 3-4 cm away from the window). Since fluorescent signal strength exponentially drops off as a function of distance, these long fluorescent signal paths lead to low signal strength when the fluorescence returns to the sensor package.

Some embodiments of the disclosure may be characterized as a fluorometer for monitoring fluorescent peaks in an analyte workspace in a liquid, comprising: an instrument assembly, the instrument assembly comprising a circuit assembly, a casing, and a window set into the casing, wherein at least a portion of the instrument assembly, including the window, is configured to be submerged within the liquid and above the analyte workspace; a buoy assembly, wherein the buoy assembly comprises a buoyancy device and a power structure, and wherein the buoy assembly is unitary with or coupled to the instrument assembly; one or more emission sources electrically coupled to the circuit assembly of the instrument assembly, wherein the one or more emission sources are configured to emit light in one or more frequencies or wavelength bands; a prism arranged in contact with the window or coupled to the window via an optical fluid or glue, wherein the prism is configured to direct emissions from the one or more emission sources towards the analyte workspace, the prism including at least one angled surface; at least one photosensor positioned above the window and configured to detect fluorescence emissions of one or more analytes being interrogated in the analyte workspace; and a filter array comprising one or more filters and positioned between the window and the photosensor, the one or more filters selected from a group consisting of a low-pass filter, a high-pass filter, and a band-pass filter.

Other embodiments of the disclosure may be characterized as method of manufacturing a fluorometer, the fluorometer comprising an instrument assembly, a circuit assembly, a power structure, and a battery, the method comprising: forming a buoy assembly, the buoy assembly having a buoyancy device, and wherein the buoyancy device is configured to float in a liquid; forming a window in the instrument assembly, wherein the window is configured to be submerged in the liquid and positioned above an analyte workspace in the liquid; coupling the buoy assembly to the instrument assembly via a watertight structural connection, the watertight structural connection selected from a group consisting of a flange, a gasket, and a fastener; nesting a portion of the instrument assembly within the buoy assembly; electrically coupling one or more emission sources to the circuit assembly of the instrument assembly, wherein the one or more emission sources are configured to emit light in one or more frequencies or wavelength bands for interrogating one or more analytes in the analyte workspace below the window, and wherein the emitted light is angled relative to a normal to the window; forming a prism having at least one angled surface, the prism shaped and positioned to direct light from the one or more emission sources towards the analyte workspace, wherein the prism is arranged to be in contact with the window and has the same or substantially the same index of refraction as the window; arranging one or more filters on an inside of the instrument assembly and in a region of the instrument assembly above the prism and the window, wherein the one or more filters are selected from a group consisting of a low-pass filter, a high-pass filter, and a band-pass filter; and arranging a photosensor above the one or more filters, wherein the photosensor is configured to be in electrical contact with the circuit assembly and detect fluorescent signal emissions associated with fluorescence of the one or more analytes in the analyte workspace.

Yet other embodiments of the disclosure may be characterized as method of monitoring fluorescent peaks in an analyte workspace in a liquid using a fluorometer, the fluorometer comprising a buoy assembly, an instrument assembly having at least a power structure, a battery, a prism, a window, one or more filters, a photosensor, and one or more emission sources, the method comprising: coupling the buoy assembly to the instrument assembly using a watertight structural connection, the watertight structural connection selected from a group consisting of a flange, a gasket, and one or more fasteners, wherein, when the fluorometer is placed in the liquid, at least a portion of the buoy assembly is configured to float above a surface of the liquid and at least a portion of the instrument assembly, including the window, is configured to be submerged below the surface of the liquid; nesting a portion of the instrument assembly within the buoy assembly; arranging one or more emission sources at an angle relative to the window, wherein the one or more emission sources are configured to transmit light or emissions; arranging the prism on an interior of the instrument assembly, wherein the prism is arranged to be in contact with the window or coupled to the window, and wherein the prism is configured to direct light from the one or more emission sources towards the analyte workspace; arranging the one or more filters on an inside of the instrument assembly and in a region of the instrument assembly above the prism and the window, the one or more filters selected from a group consisting of a low-pass filter, a high-pass filter, and a band-pass filter; arranging a photosensor above the one or more filters, wherein the photosensor is configured to be in electrical contact with the circuit assembly; placing the fluorometer in the liquid; transmitting, from the one or more emission sources, light or emissions for interrogating one or more analytes in the analyte workspace located below the window; and detecting fluorescent signal emissions associated with fluorescence of the one or more analytes in the analyte workspace based at least in part on the transmitting.

BRIEF DESCRIPTION OF DRAWINGS

Various objects and advantages, and a more complete understanding of the present disclosure, are apparent and more readily appreciated by referring to the following detailed description and to the appended claims when taken in conjunction with the accompanying drawings:

FIG. 24 shows an alternative embodiment of a fluorometer, in accordance with one or more implementations;

DETAILED DESCRIPTION

Figure 1A:
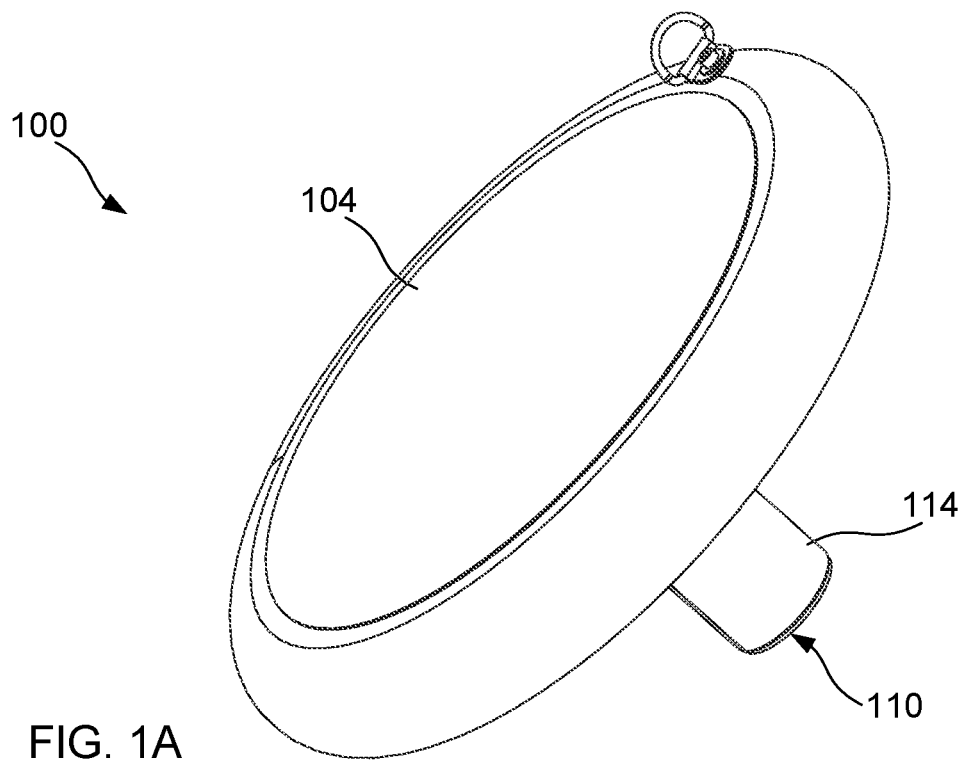
FIG. 1A illustrates an isometric view of a fluorometer according to an embodiment of this disclosure.

The words "for example" are used herein to mean "serving as an example, instance, or illustration." Any embodiment described herein as "for example" are not necessarily to be construed as preferred or advantageous over other embodiments.

Preliminary note: the flowcharts and block diagrams in the following Figures illustrate the architecture, functionality, and operation of possible implementations of systems, methods and computer program products according to various embodiments of the present invention. In this regard, some blocks in these flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

As previously noted, harmful algal blooms (HABs) exert strongly negative impacts on coastal oceans, lakes, rivers, and municipal drinking supplies world-wide. For instance, not only are HABs harmful for human consumers, but the toxic blooms are often devastating to the ecosystem and to a large variety of marine organisms. Despite the danger posed by HABs, current techniques for monitoring HABs are lacking. Devices for monitoring fluorescent peaks for HAB as well as other harmful substances in water bodies in use today tend to either be hand-held, lab-based, or buoy-based. While lab-based systems may be effective at identification, the challenge of continuously providing water samples to a remote lab limits their effectiveness for continuous water monitoring. Hand-held systems are overly-labor dependent, do not allow 24-7 monitoring, and are more difficult to use more than a few feet from shore. Buoy-based systems overcome the challenges of lab-based and hand-held systems but tend to include sensors that probe more than thirty inches below the surface, despite the majority of plankton activity occurring within twelve inches of the surface. Additionally, most sensing systems use a transparent window to separate electrical components from water, and this window greatly reduces light transmission because of total internal reflection (TIR), unless emissions are made relatively close to perpendicular to the window. However, this need to avoid TIR leads to fluorescent stimulation far below the window surface (e.g., emissions intersecting a normal to the window at a center of the sensor at 3-4 cm away from the window). Since fluorescent signal strength exponentially drops off as a function of distance, these long fluorescent signal paths lead to low signal strength when the fluorescence returns to the sensor package.

Figure 8:
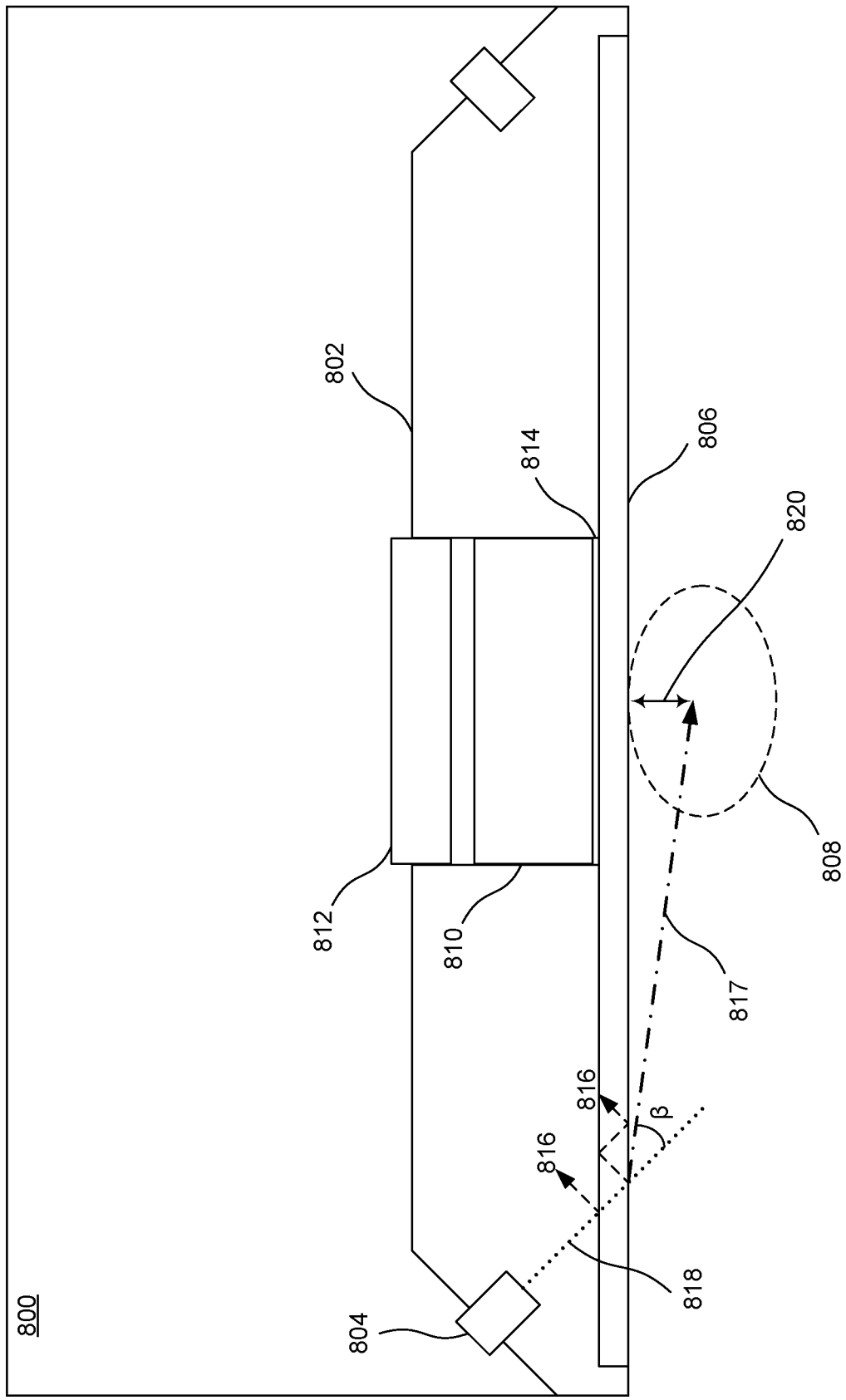
FIG. 8 illustrates one embodiment of an instrument assembly, in accordance with one or more implementations.

Thus, there is a need for a submersible fluorometer and/or turbidity sensor that is able to reduce the stimulation angle (or increase the angle from the vertical), while avoiding losses to TIR, to thereby achieve fluorescence emissions closer to the sensor package (e.g., ~1 cm or less for distance 820 in FIG. 8). In some aspects, a fluorometer that is able to achieve fluorescence emissions closer to the sensor package may also facilitate in enhancing fluorescent signal strength at the photosensor. As described later with reference to FIG. 8, the distance 820 is measured between the window 806 and an intersection of the emissions (dotted line below window 806) and a normal to the window 806 at a center of the photosensor 812.

For the purposes of this disclosure, the analyte workspace is a region below the window of the instrument assembly where one or more analytes are being interrogated.

Figure 1B:
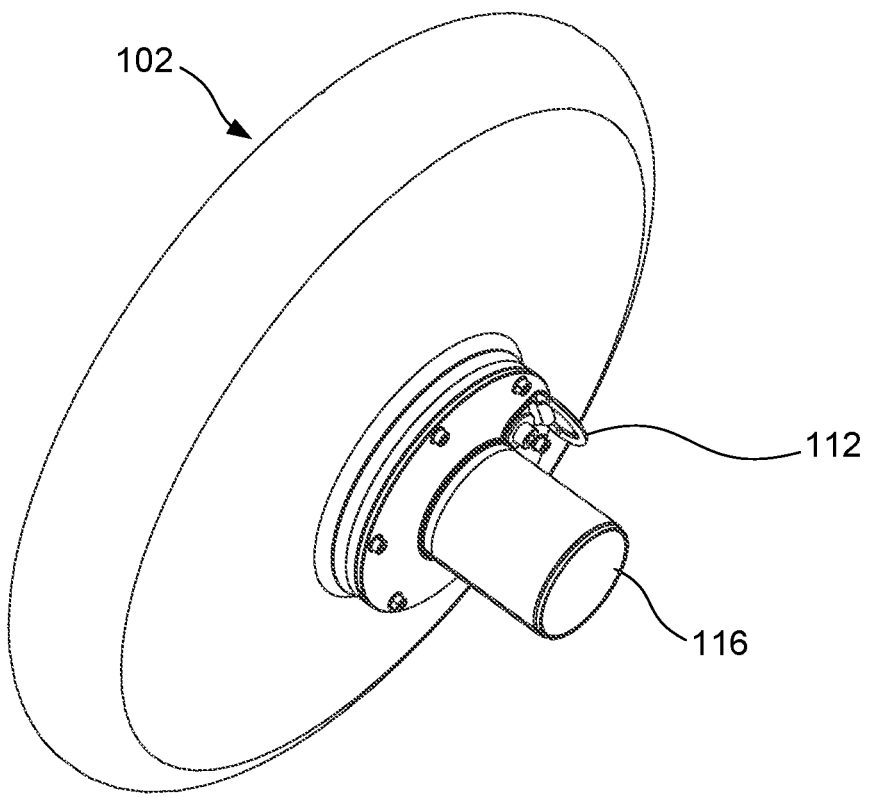
FIG. 1B illustrates an isometric view of the fluorometer in FIG. 1A according to an embodiment of this disclosure.

FIGS. 1A and 1B illustrate two isometric views of a fluorometer 100 according to an embodiment of this disclosure. In some examples, the fluorometer 100 can include a buoy assembly 102 and an instrument assembly 110. Furthermore, the buoy assembly 102 may include a buoyancy device, such as the disc-shaped hollow component illustrated in FIGS. 1A and 1B. In some embodiments, the buoyancy device 104 may comprise a watertight structure filled with air or another composition that is less dense than water, such as oil. In some cases, the buoyancy device may be shaped and sized such that its width or diameter is greater than its height. As shown, the buoyance device has a much greater width or diameter than its height. The use of such a shape for the buoyance device 104 may serve to provide stability to the fluorometer in rough water and waves, windy conditions, high tide, etc., as well as stabilize measurements in calm water. In some embodiments, the buoy assembly 102 may further comprise a power structure, such as the solar assembly 104 seen in FIG. 1. Other types of power structures are contemplated in different embodiments. For instance, in some cases, the buoy assembly may comprise a power structure configured to harness energy from the waves and/or wind. In some cases, the buoy assembly 102 may also include a battery for storing energy from the power structure (or the battery can reside in the instrument assembly 110). The buoy assembly 102 can be coupled to the instrument assembly 110 via a watertight structural connection 108. In some cases, the watertight structural connection may be selected from a group consisting of a flange, gasket, and one or more fasteners, although any other structure capable of providing a watertight connection may be utilized in different embodiments. Alternatively, the buoy assembly 102 and the instrument assembly 110 may be formed as a single monolithic assembly (see FIG. 24). In other words, in some embodiments, the buoy assembly 102 may be unitary with or coupled to the instrument assembly 110 without seams between these two assemblies. As illustrated, the fluorometer 100 may further include an anchoring point 112, which can be any type of hook, loop, or other attachment structure to which an anchor can be affixed.

In some cases, the instrument assembly 110 may comprise one or more of a casing 114, a window 116, and internal components to be discussed relative to subsequent figures. The illustrated instrument assembly 110 couples to a bottom of the buoy assembly 102. However, to locate the instrumentation within the instrument assembly closer to a surface of the water, the buoy assembly 102 may comprise an opening or depression in its bottom, which may allow a portion of the instrument assembly 110 to be nested within the buoy assembly 102 and thereby move the window 116 up toward a surface of the water.

Figure 2A:
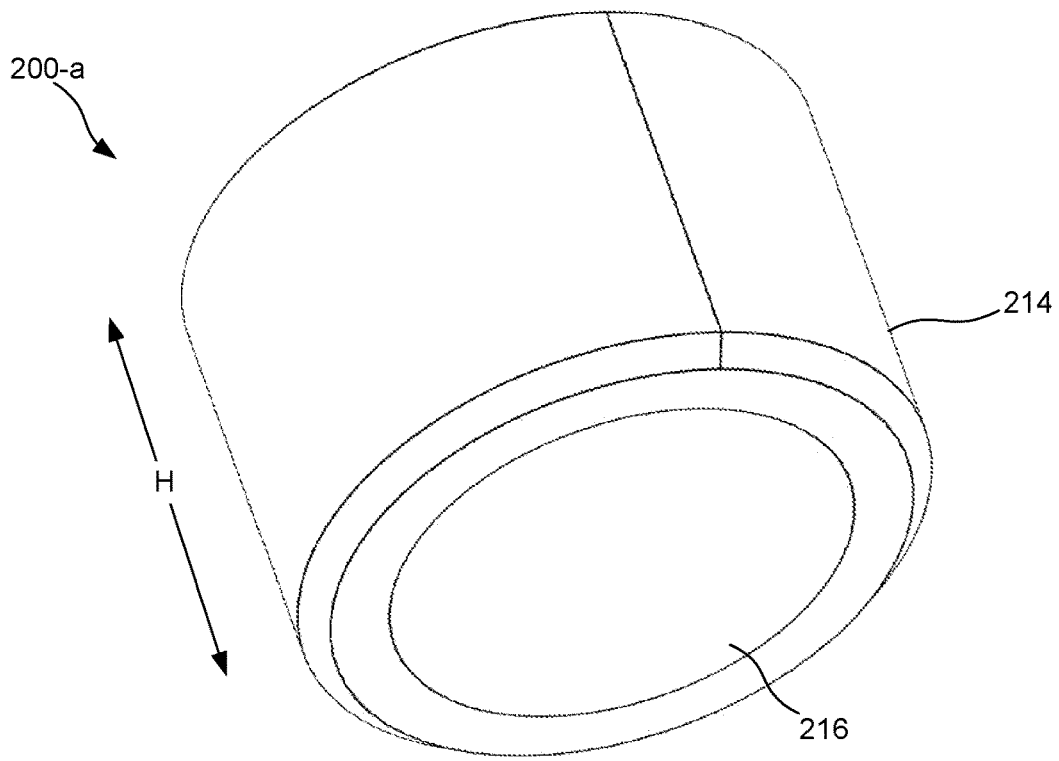
FIG. 2A illustrates an isometric view of an instrument assembly of the fluorometer in FIG. 1A according to an embodiment of this disclosure.
Figure 2B:
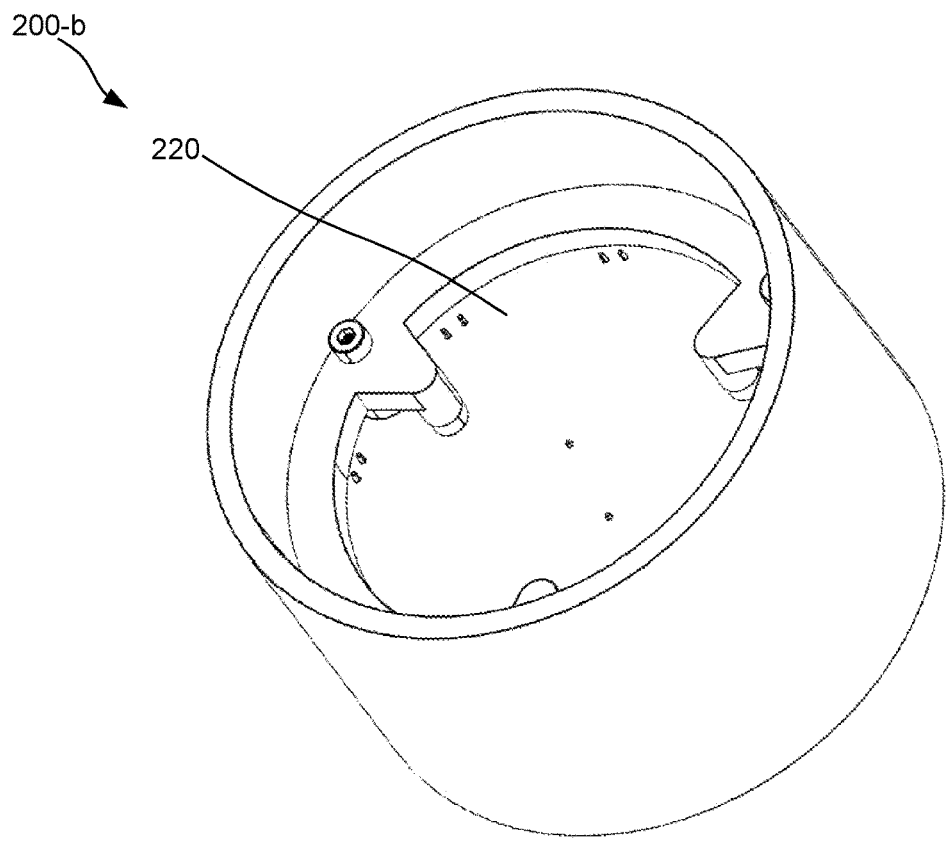
FIG. 2B illustrate an isometric view of an instrument assembly of the fluorometer in FIG. 1A according to an embodiment of this disclosure.

FIGS. 2A and 2B illustrate two isometric views 200-a and 200-b, respectively, of an embodiment of the instrument assembly 110 seen in FIGS. 1A and 1B. Here, a window 216 is set into a casing 214 and a gasket between the two forms a watertight seal. Inside the casing 214 is a circuit board or circuit assembly 220 that can be coupled to light sources, logic circuits, memory, a power storage component (e.g., a battery), and photosensor, to name a few non-limiting examples. This arrangement as well as the optics used (discussed in detail later) allow a more compact package (e.g., shorter H) than seen in the art, and this allows stimulation closer to the water's surface.

Figure 3:
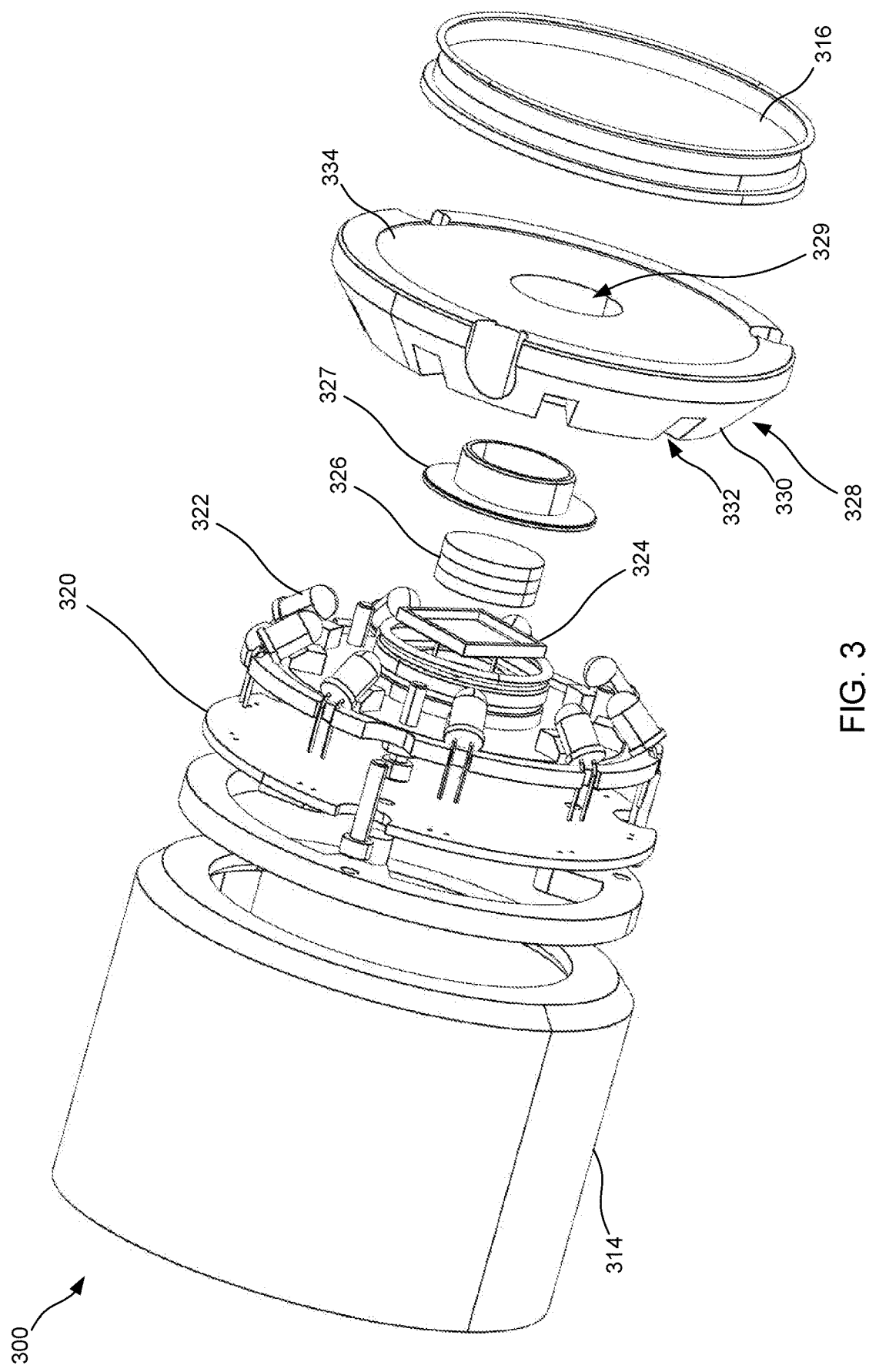
FIG. 3 shows an exploded view of the instrument assembly of FIGS. 2A and 2B, according to an embodiment of this disclosure.

FIG. 3 shows an exploded view of the instrument assembly of FIGS. 2A and 2B. As seen, FIG. 3 illustrates an instrument assembly 300, which may be similar or substantially similar to the instrument assembly 110 shown in FIGS. 1A and 1B. In some cases, instrument assembly 300 comprises a casing 314, a window 316, and a circuit board or circuit assembly 320. Furthermore, instrument assembly 300 may also comprise one or more emission sources (e.g., LEDs) 322, where the one or more emission sources may be configured to be electrically coupled to the circuit assembly 320. In some examples, the one or more emission sources 322 may be angled relative to the window 316. For instance, in the example shown, the emission sources 322 are angled inward toward a central axis of the instrument assembly 300, but in other embodiments they can be arranged at different angles and even angled outward such that the stimulating emissions reflect off a reflective coating/surface on the inside of the casing 314 (see related discussion in FIGS. 16-21, for instance).

In some cases, the instrument assembly 300 may also comprise a photosensor 324, which may be in electrical contact with the circuit assembly 320. In some cases, the photosensor 324 may be aligned with the central axis of the instrument assembly and perpendicular to the window 316. Additionally, the instrument assembly 300 may also comprise a filter array 326 having one or more filters between the window 316 and the photosensor 324.

Figure 4:
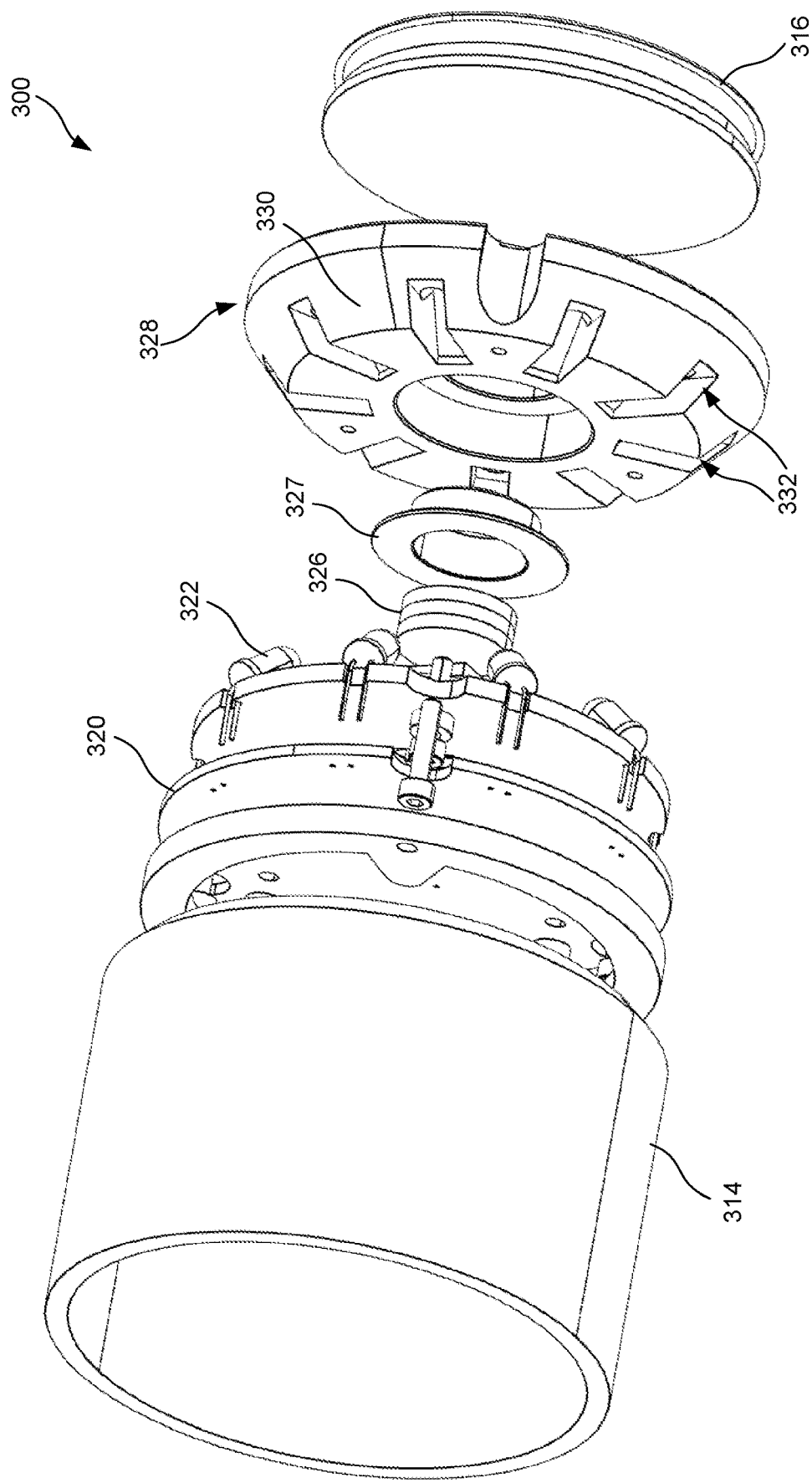
FIG. 4 shows a detailed view of the instrument assembly of FIGS. 2A and 2B, according to an embodiment of the disclosure.
Figure 5:
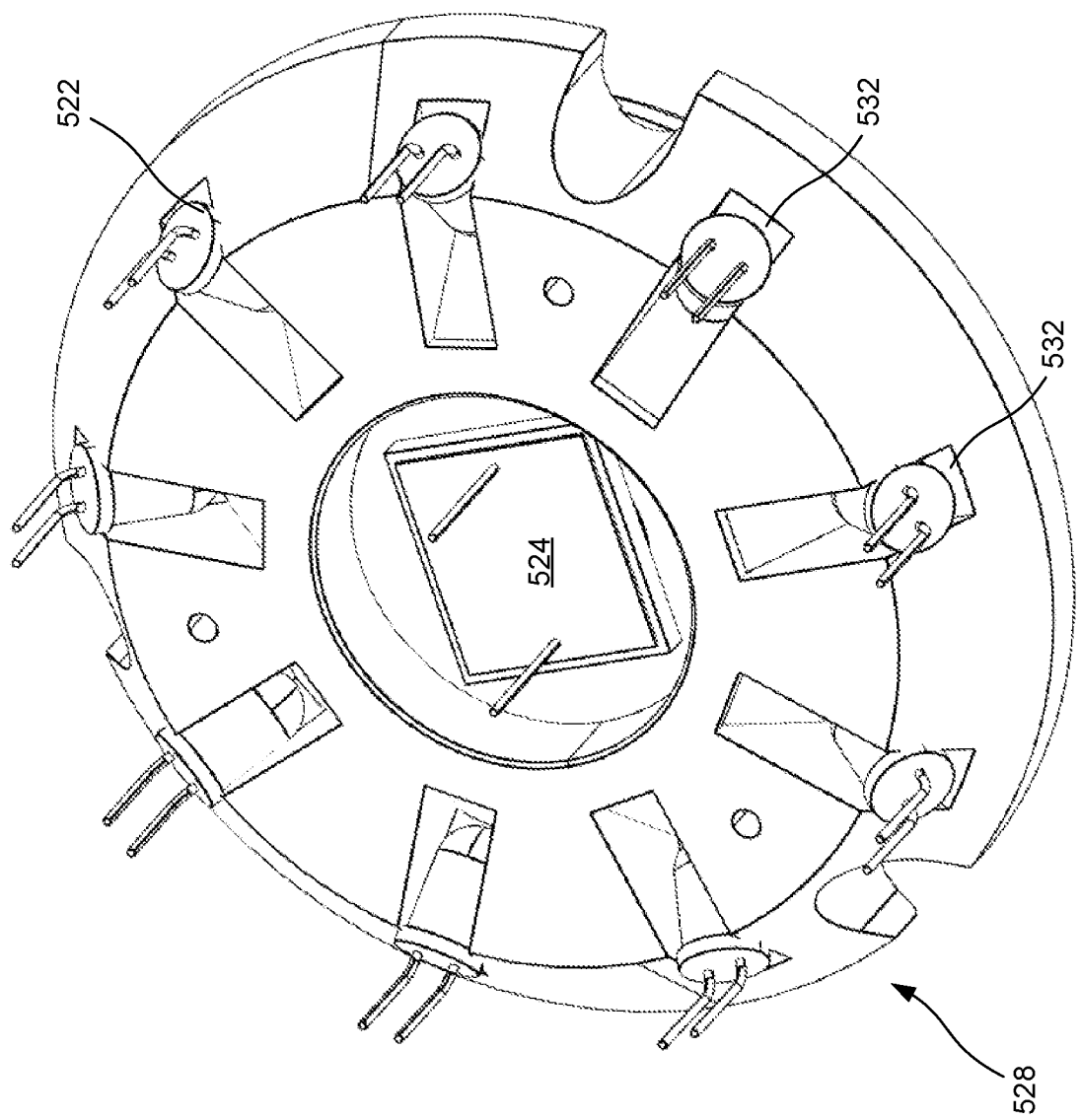
FIG. 5 shows a detailed view of a prism assembly including emission sources, according to an embodiment of the disclosure.
Figure 9:
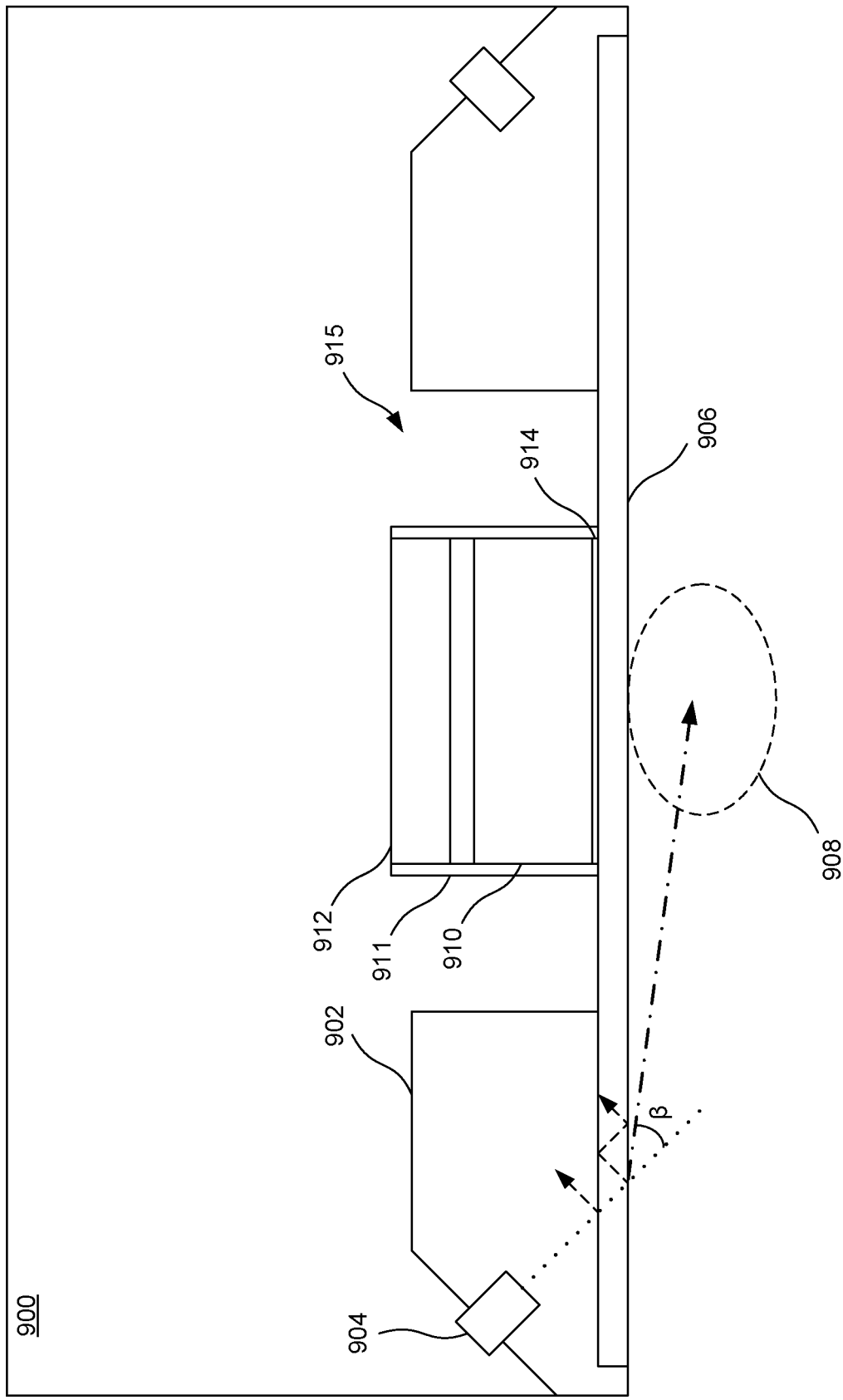
FIG. 9 illustrates another embodiment of an instrument assembly, in accordance with one or more implementations.

In some embodiments, the instrument assembly 300 may also include a prism 328 having one or more angled surfaces 330. In some circumstances, these angled surfaces 330 may help prevent (or reduce) light from the emission sources 322 from reflecting off a top surface of the window 316. In this way, by reducing reflection off the window 316, a higher proportion of light or emissions may reach the analyte workspace, which may serve to enhance identification of HABs. Along these same lines, the one or more angled surfaces 330 of the prism 328 can also lead to reflections. In some cases, the amount of reflection from the angled surfaces 330 may be proportional to the angle between the emissions from the emission sources 322 and a line or axis perpendicular to the angled surface 330. In other words, the reflections off of the angled surfaces may increase as the angle of incidence of the emissions increases. Accordingly, the angled surface 330 should be selected so as to be perpendicular with an angle of incidence of a majority of emissions from the emission sources 322. However, as will be discussed relative to FIG. 12, there may be situations where the emission sources 322 and angled surfaces 330 are not perfectly aligned. To mitigate the effects of such situations, the prism 328 may include indentations 332 for each of the emission sources 322, where these indentations 332 may include additional angled surfaces to minimize reflections from the emission sources 322 (e.g., by being aligned with a primary incidence angle from the emission sources 322). FIG. 9 shows a schematic view of such an alignment. FIG. 4 shows another view of the indentations 332. FIG. 5 described later shows one or more emission sources 522 arranged in a prism 528. In another embodiment, the emission sources 322 can be embedded in the prism 328 during fabrication (e.g., the prism 328 can be molded around the emission sources 322, or the emission sources 322 can be included in an injection mold used to manufacture the prism 328).

Returning to FIG. 3, the filter assembly 326 may be shaped and sized to fit within a filter housing 327, where the inner surface of the filter housing 327 can have a reflective inner surface. Alternatively, in lieu of the filter housing 327, the inner surface of an annular aperture 329 in the prism 328 can be reflective.

In some embodiments, the window 316 may be coupled to the prism 328 via an optical fluid or adhesive, which may serve to ensure that there are no air gaps between these two components. In the illustrated embodiment, the prism 328 can also include an indentation or depression 334 into which a portion or all of the window 316 can be arranged. In some examples, the window 316 can be formed from sapphire, glass, or fused silica, to name three non-limiting examples. Other materials with adequate transparency and/or low reflective properties may also be used to form the window 316 in different embodiments. In some embodiments, the prism 328 can be formed from the same material used to form the window 316. Alternatively, the prism 328 can be formed from a material, such as polycarbonate, having a similar index of refraction as the material used to form the window 316. Those of skill in the art will appreciate that interfaces between materials of significantly different indices of refraction (e.g., air and glass) may be prone to greater levels of reflection, for instance, in the form of Total Internal Reflection (TIR). TIR may refer to a complete reflection of light within a medium such as water or glass when light waves incident from within the medium reflect off the boundary with a medium having a lower density, such as air. Two conditions necessary for TIR to take place include: light traveling from a more-dense medium (e.g., glass) to a less dense medium (e.g., air), and the angle of incidence at the boundary between the two mediums being greater than the critical angle, further discussed in FIG. 13. Thus, to reduce reflections, and maximize the emissions reaching the analyte workspace, the window 316 and prism 328 should be selected from materials that reduce reflections off the prism-to-window interface (i.e., the window 316 and the prism 328 should have substantially similar indices of refraction to prevent reflections).

The emission sources 322 can include one or more LEDs or other sources. Further, the one or more emissions sources 322 may be configured to emit light in one or more different frequencies or wavelength bands. For instance, the sources 322 can include a plurality of LEDs operating at blue frequencies, for instance at or near 490 nm. In some cases, the wavelength or wavelength bands of the emission sources 322 can be selected to coincide with an absorption or fluorescence band or peak for an analyte in the liquid (e.g., water) being interrogated. In some cases, the filter assembly 326 may comprise at least one of a high pass filter, a low pass filter, or a band pass filter. In some embodiments, the filter assembly 326 may be configured to block or absorb all light below a given wavelength, such as 610 nm, or below a lower wavelength threshold for fluorescence of the analyte. As an example, algae may fluoresce at 670 nm, and thus the filter assembly 326 can be selected to absorb a majority of light below 610 nm (i.e., the filter assembly may comprise a high pass filter with a cutoff frequency at 610 nm). In another example, algae may fluoresce between 650 nm and 680 nm, and thus the filter assembly may be selected to absorb a majority of light below 620 nm and above 700 nm (i.e., the filter assembly may comprise a band pass filter to pass light between 620 nm and 700 nm). Alternatively, in this example, the filter assembly may be selected to block or absorb all light below the lower wavelength threshold for fluorescence (i.e., 650 nm), and a high pass filter with a cutoff frequency at 610 or 620 nm could be utilized instead. In some other cases, fluorescence occurs at multiple wavelengths, and the emission sources 322 and filter assembly 326 can be selected to accommodate these multi-band analytes, for instance, via a combination of high pass, low pass, and/or band pass filters, as well as LEDs configured to light in different wavelengths or bands (e.g., green LEDs, blue LEDs, etc.). In yet other cases, a band reject filter may be utilized in the filter assembly 326. In some embodiments, analysis algorithms may be used to help identify the component fluorescing, for instance, if the width of the fluorescence band is above a threshold (e.g., 50 nm, 100 nm, etc.).

FIG. 4 shows a detailed view of the instrument assembly 300 of FIG. 3, according to an embodiment of the disclosure.

Further, FIG. 5 shows a detailed view of an instrument assembly 500 comprising a prism 528, according to an embodiment of the disclosure. As shown, the prism 528 comprises one or more emission sources 522 installed in one or more indentations 532 around a perimeter of the prism 528. In some cases, the instrument assembly 500, the prism 528, and the one or more emission sources 522 may be examples of the instrument assembly 300, the prism 328, and the one or more emission sources 322 previously described in relation to FIG. 3. In some cases, the instrument assembly 500 may further comprise a photosensor 524, which may be similar or substantially similar to the photosensor 324 describe in relation to FIG. 3. In some cases, the photosensor 524, may be in electrical contact with a circuit board or assembly (not shown here, but shown as circuit assembly 320 in FIG. 3) and may be positioned such that it is aligned with the central axis of the instrument assembly 500 and perpendicular to the window (shown as window 316 in FIG. 3). As previously noted, the instrument assembly 500 may also comprise a filter array having one or more filters between the window and the photosensor 524. In this way, the light or emissions arriving at the photosensor 524 from the analyte workspace below the window may be restricted to the frequencies of concern (i.e., corresponding to a wavelength band or bands for fluorescent peaks of analytes). Some examples of analytes may include green algae, chlorophyll, phytoplanktons, cyanobacteria, marine biotoxins (e.g., microcystin, cylindrospermopsin, etc.), other pigments associated with HABs, heavy metals, and/or dissolved organic matter (DOM), to name a few non-limiting examples.

In some embodiments, the photosensor 524 may be in electronic communication with a fluorescence processor (not shown). The fluorescence processor may be on-site (i.e., within the fluorometer) or off-site (i.e., at a remote location). If off-site, the fluorometer may comprise a wireless transmitter to transmit fluorescence information associated with the fluorescence emissions from the analyte workspace to the remote fluorescence processor, where the fluorescence information may be received from the photosensor 524. In some cases, the fluorescence information may comprise at least a wavelength and a magnitude of fluorescence peaks, and the fluorescence processor may be configured to identify the one or more analytes based at least in part on correlating the fluorescence information to known fluorescent signatures of algal blooms, for instance. If on-site, the fluorescence processor of the fluorometer or instrument assembly 500 may analyze the fluorescence information received from the photosensor 524 and identify the one or more analytes, following which it may transmit an indication of the identified analytes to a control center or administrator located off-site. In some cases, the fluorescence processor may be configured to send an indication of the identified analytes, for instance, if the concentration in the water source exceeds a threshold (e.g., >1 mg/l for green algae, >4 mg/l for cyanobacteria, >0.4 ug/l for Mycrocystin, >4 nanomolar for Mercury, to name a few non-limiting examples). In other cases, no threshold may be set, and the fluorescence processor may be configured to send an indication of any detected analyte(s).

Figure 6:
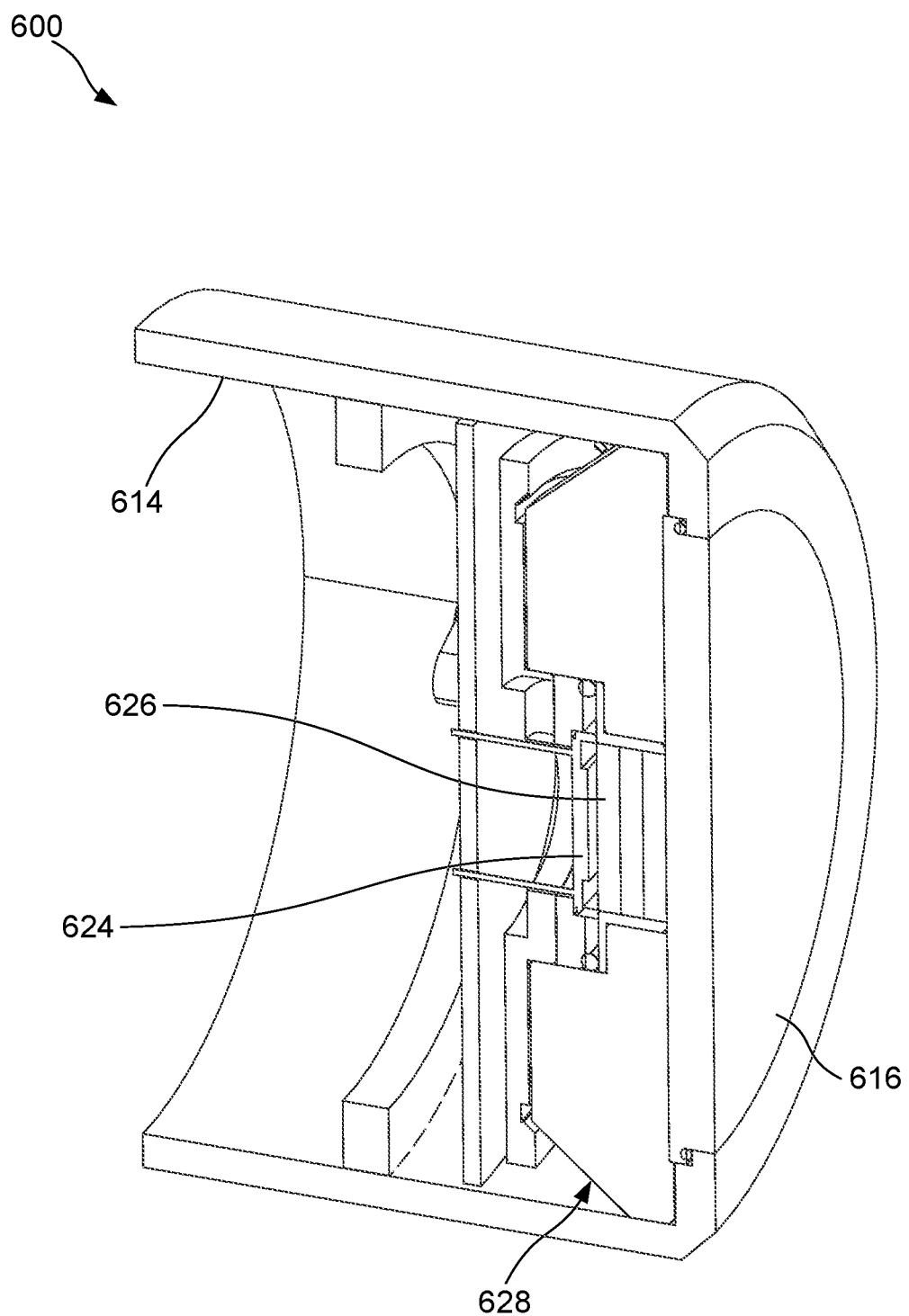
FIG. 6 shows a cross section of an embodiment of the instrument assembly in accordance with one or more implementations.

FIG. 6 shows a cross section of an embodiment of an instrument assembly 600. Instrument assembly 600 may be similar or substantially similar to one or more of instrument assembly 200, 300, and 500. As shown, instrument assembly 600 comprises a casing 614, a window 616, a prism 628, at least one photosensor 624, and a filter assembly 626 positioned between the window 616 and the photosensor 624. In this embodiment, three filters make up the filter assembly 626, though other numbers of filters may also be implemented. Similar to instrument assemblies 300 and 500, the photosensor 624 of the instrument assembly 600 may be in electrical contact with a circuit board or assembly and may be positioned such that it is aligned with the central axis of the instrument assembly 600 and perpendicular to the window 616. In some cases, the photosensor 624 may be configured to pass fluorescence information to a fluorescence processor (not shown), where the fluorescence information may comprise at least a wavelength and a magnitude of fluorescence peaks. Furthermore, the fluorescence processor may be configured to identify the one or more analytes being interrogated in the analyte workspace below the window 616, where the identification may be based at least in part on correlating the fluorescence information to known fluorescent signatures of algal blooms, for instance. In some cases, the analyte workspace may extend to 1 cm below the window and within the liquid (e.g., lake or river water) where the fluorometer comprising the instrument assembly 600 is installed, although other distances for the analyte workspace are contemplated in different embodiments.

Figure 7:
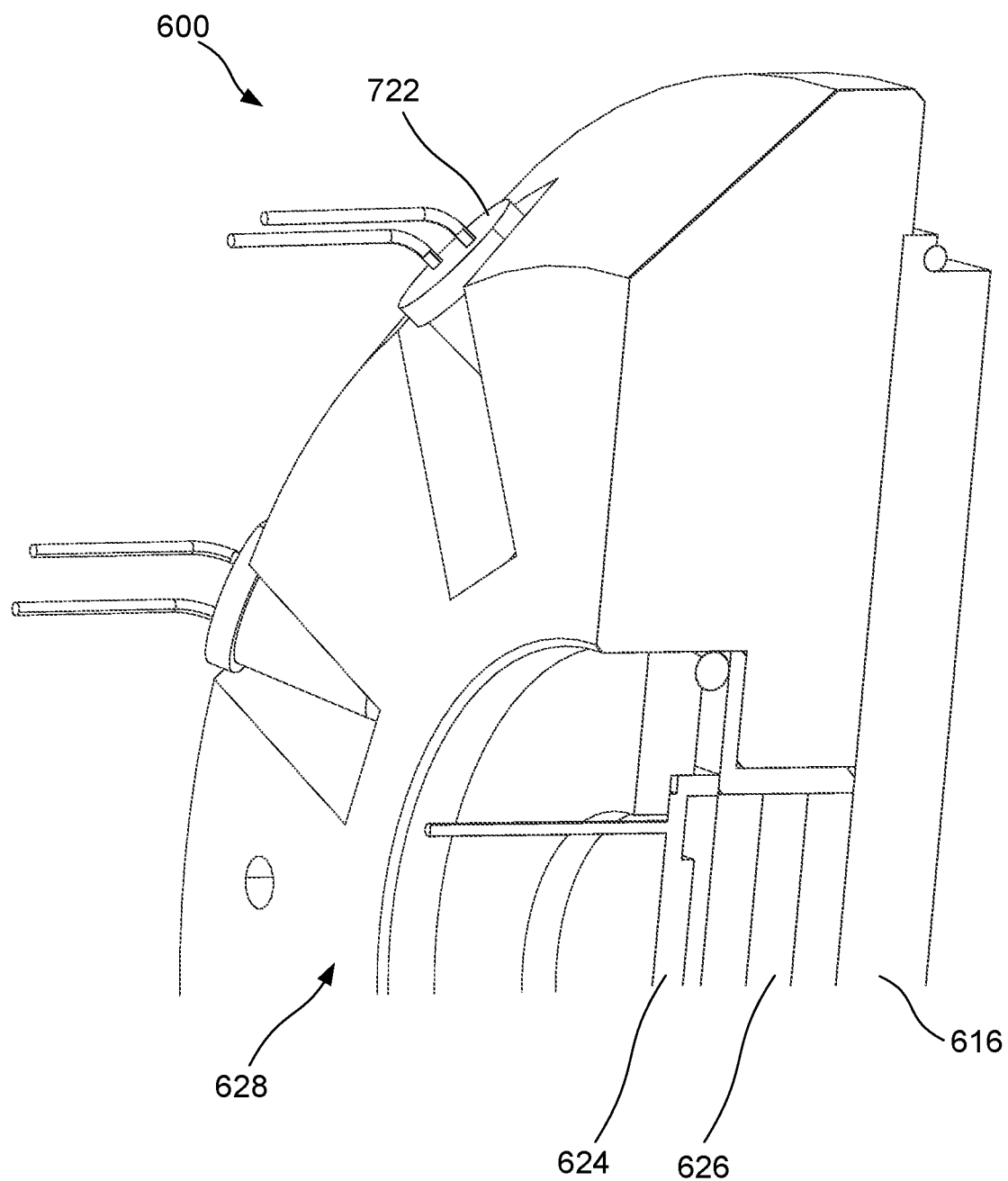
FIG. 7 shows a closer view of the cross section of FIG. 6, in accordance with one or more implementations.

FIG. 7 shows a closer view of the cross section of the instrument assembly 600 in FIG. 6, but only showing the window 616, filter array 626, prism 628, and photosensor 624. Furthermore, the instrument assembly 600 in FIG. 7 also illustrates one or more emission sources 722 arranged to be contact with the prism 628 (e.g., the emission sources are embedded or molded into the prism). In some cases, emissions from the one or more emission sources 722 may bend toward the analyte workspace below the window when the emissions intersect the bottom of the window 616 or an interface between the window 616 and the liquid (e.g., water). As previously noted, in some cases, an index of refraction of the prism 628 may be the same or approximately the same as an index of refraction of the window. For instance, the window 616 may be formed using sapphire, glass, or fused silica, and the prism 628 may also be formed using sapphire, glass, or fused silica. Alternatively, the prism 628 may be formed using a polycarbonate having a similar index of refraction as the window.

FIG. 8 illustrates an embodiment of an instrument assembly 800. The instrument assembly 800 may be similar or substantially similar to any of the instrument assemblies described herein, such as instrument assembly 300 or 600. As shown, the instrument assembly includes a prism 802, a plurality of emission sources 804, such as LEDs, a window 806, an analyte workspace 808 below the window 806, a filter assembly 810, an air gap 814 between the window 806 and the filter assembly 810, and a photosensor 812. The emission sources 804 can be embedded in the prism 802 such that little to no reflection takes place at a source-to-prism interface. FIG. 8 shows that the initial emission 818 is partially transmitted (e.g., transmission 817 shown by the dash-dot line) and partially reflected (e.g., reflection 816 shown by the dashed line) at the prism-to-window interface. This disclosure uses a prism 802 arranged in contact with the window 806, where both the prism 802 and the window 806 have relatively the same indices of refraction (or the same index of refraction), such that a much shallower or lower angle can be used for the emission sources 804 than in the prior art, while still minimizing the portion of emissions that are reflected and maximizing the transmitted emissions. In some cases, the use of such a structure for the instrument assembly 800 may achieve distances (i.e., measured as distance 820) of around or less than 1 cm between the analyte workspace 808 and the bottom of the window 806. In some examples, this distance 820 may be measured from a center of the analyte workspace 808, where the analyte workspace has an elliptical shape.

In some cases, as the emission 818 hits the bottom of the window 806, or the window-to-liquid interface, the emission 818 tends to bend inward toward the analyte workspace 808. In some cases, this bending may be enhanced by the shallower angle of the emission source(s) 804 relative to the window 806. While there is little if any bending at the prism-to-window interface, due to the similarity (or equivalence) of the indices of refraction and lack of air gap therebetween, emission 818 may nonetheless depart from this initial path of incidence by an angle β after passing into the liquid (i.e., due to the liquid having a different index of refraction than the prism and/or window).

Furthermore, as shown, some reflections 816 off the bottom of the window 806, or the window-to-liquid interface, may return to the prism 802, bounce around one or more times within the window 806 as a byproduct of TIR, or bounce around and then exit into the liquid. In some circumstances, some of these reflections 816 can enter the filter assembly 810. Since these internally-reflecting rays have not interrogated the analyte, they are not desired. To mitigate these stray rays, the filter assembly 810 may be positioned such that there is an air gap 814 between the filter assembly 810 and the window 806, and this air gap may help keep the stray light 816 within the window 806 (i.e., since any interface with a substantial change in index of refraction, for instance, from glass to air, is more likely to cause reflection than transmission, especially for large angles of incidence). In some cases, a portion of these TIR reflections 816 may reach ends of the window 806 and subsequently return toward the middle (e.g., above the analyte workspace) after reflecting off of the ends. In an embodiment, the ends of the window 806 may be painted or coated with a light-absorbing material (e.g., vantablack or flock paper, to name two non-limiting examples) or a black paint/pigment. Additionally or alternatively, the ends of the window 806 may be textured, sandblasted, or otherwise roughed up to further to reduce stray light reflections back down the window 806. In some other cases, the sides of the filter assembly 810 and/or sides of the prism 802 (i.e., where the prism 802 meets the filter assembly 810) may include a reflective surface or housing to help light (i.e., the fluorescent emissions) passing through the filter assembly 810 to reflect and arrive at the photosensor 812. In other words, the reflective surface on the sides of the filter assembly 810 and/or the prism 802 may serve to confine light (i.e., the fluorescent emissions) above the window and direct it towards to the photosensor 812.

In some circumstances, the window-to-liquid interface may experience the greatest losses to reflections since the difference in the index of refraction is larger than, for instance, at the prism-to-window interface. In some embodiments, a bottom of the window 806 may be coated, for instance, with an anti-reflection coating or anti-reflection layers, which may help reduce reflections within the window 806 and encourage transmission into the liquid.

It should be noted that, FIG. 8 is illustrative only and other arrangements of the components shown therein can be implemented for not only achieving a high degree of transmission to the analyte workspace, but also ensuring that the analyte workspace is positioned as close to the window as possible (e.g., <1 cm, <2 cm, etc.). For instance, FIG. 9 shows an alternative arrangement where a prism 902 includes a wider annular aperture 915 around filter array 910 and photosensor 912. In this case, since the edges of the annular aperture 915 are not pressed up against the filter array 910 and the photosensor 912, a coating or filter housing 911 having a reflective internal surface may be utilized. In some cases, the filter housing 911 may be shaped and positioned to wrap around the filter array 910 and/or the photosensor 912. Additionally, the reflective internal surface of the filter housing 911 may serve to minimize fluorescence emissions from leaking out of a path to the photosensor 912 after passing into the filter assembly 910 from the analyte workspace 908. Similar to FIG. 8, the instrument assembly 900 in FIG. 9 may also comprise one or more emission sources (e.g., LEDs) 904, a window 906, an air gap 914 between the filter assembly 910 and the window 906, and an analyte workspace 908 below the window.

Figure 10:
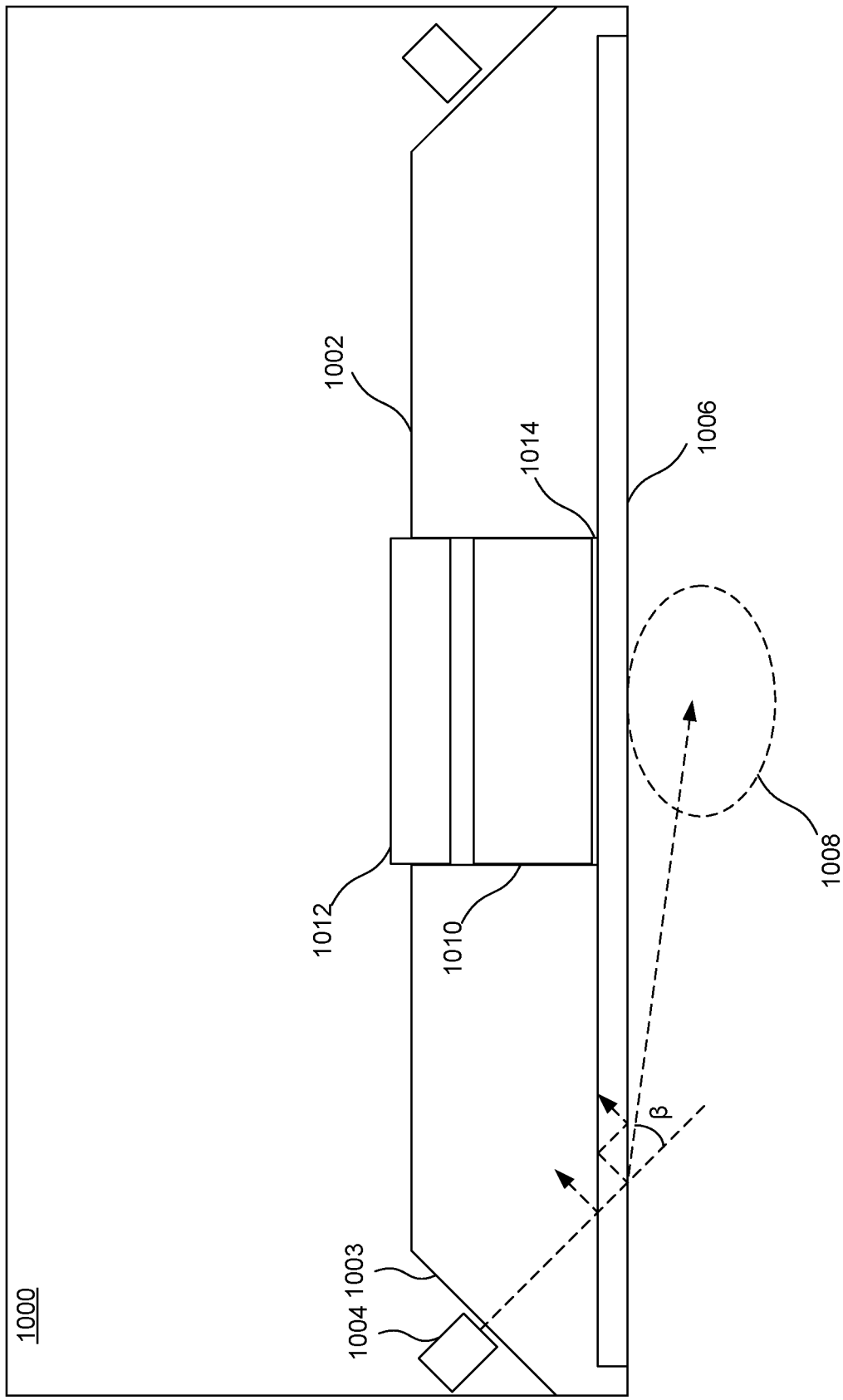
FIG. 10 illustrates an alternate embodiment of an instrument assembly, in accordance with one or more implementations.

FIG. 10 illustrates an instrument assembly 1000, which may be similar or substantially similar to the instrument assembly 800 in FIG. 8. Instrument assembly 1000 comprises a prism 1002, a window 1006, one or more emission sources 1004, a filter assembly 1010, an air gap 1014 formed between the window 1006 and the filter array or assembly 1010, and a photosensor 1012. Further, FIG. 10 also illustrates an analyte workspace 1008 below the window 1006, where the analyte workspace 1008 is a region in the liquid where one or more analytes are being interrogated.

FIG. 10 shows that the emission sources 1004 do not have to be embedded in the prism 1002 and can instead be spaced from the prism 1002. For instance, the emission sources 1004 may be spaced from an angled surface 1003 of the prism 1002. In other words, the emission sources 1004 may be arranged such that there is an air gap between the emission sources 1004 and the angled surface 1003. In such cases, the emission sources 1004 may also be arranged and positioned such that the angle of incidence of a main beam of the emissions (or an angle of light having the greatest intensity) may be perpendicular to the angled surface 1003. Such an arrangement of the emission sources 1004 may serve to reduce losses to reflections at this angled surface 1003. For the purposes of this disclosure, an angle of incidence of emissions from an emission source may refer to an angle of incidence for emission(s) that are normal or perpendicular to the emission source. In other words, since the emission sources are LEDs or other light sources that emit at a variety of angles, the angle of incidence generally refers to the angle of incidence for emissions that are perpendicular (rather than at an angle) to the emission source (or that angle comprising the greatest intensity of emitted light).

Figure 11:
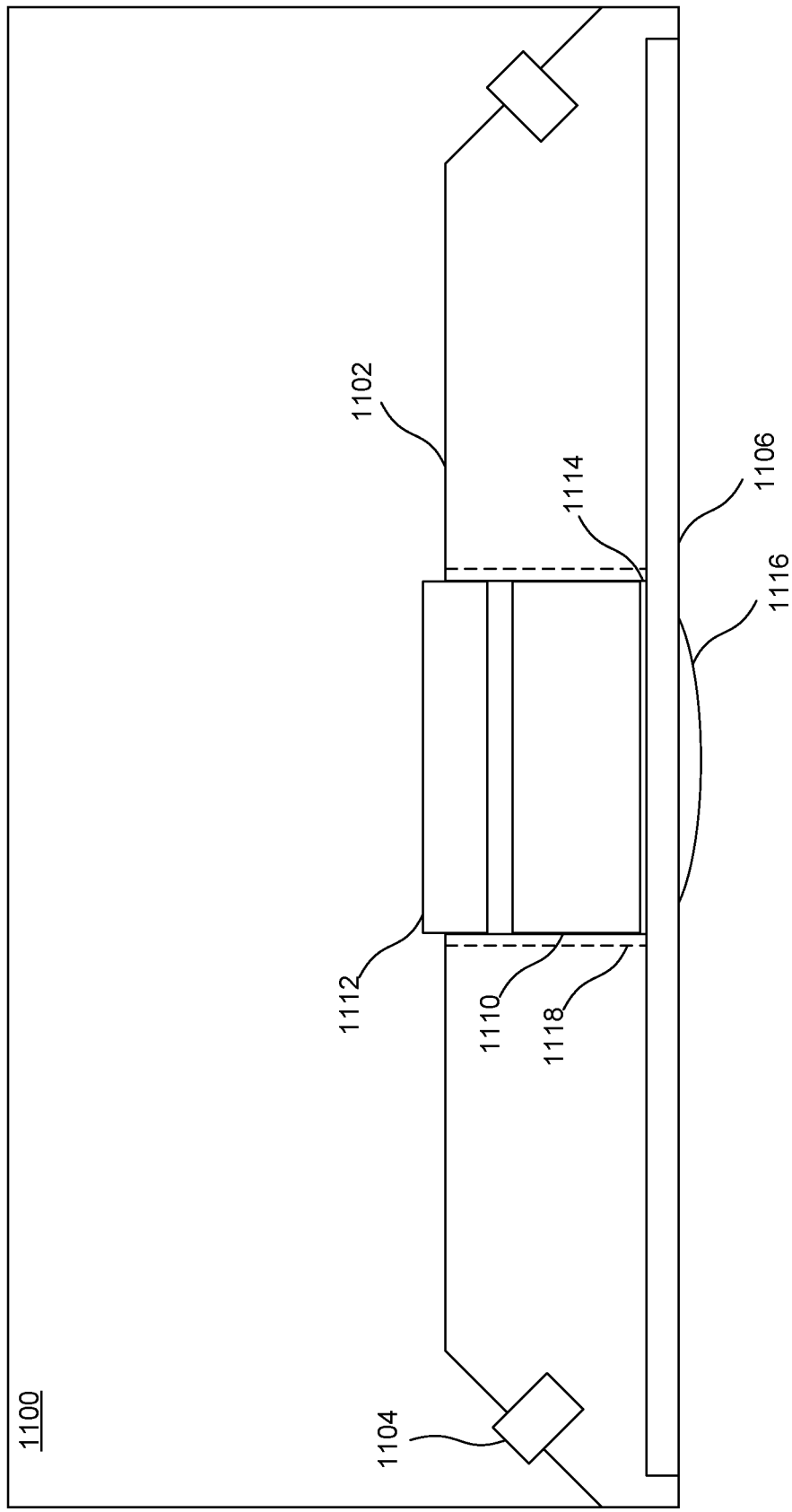
FIG. 11 illustrates an alternate embodiment of an instrument assembly, in accordance with one or more implementations.

FIG. 11 illustrates an instrument assembly 1100, which may be similar or substantially similar to the instrument assembly 800 and/or instrument assembly 1000 in FIG. 8 and/or 10, respectively. Instrument assembly 1100 comprises a prism 1102, a window 1106, one or more emission sources 1104, a filter assembly 1110, an air gap 1114 formed between the window 1106 and the filter array or assembly 1110, and a photosensor 1112. While not shown, FIG. 11 also includes an analyte workspace below the window 1106, similar to the analyte workspace 1008 in FIG. 10, for instance. FIG. 11 shows an embodiment of an instrument assembly where a convex or focusing lens 1116 may be arranged to a bottom of the window 1106, which may help direct fluorescence emissions from the analyte workspace to the photosensor 1112. FIG. 11 also shows that a housing 1118 with a reflective inner surface, or a reflective coating on an inside edge of an annular aperture of the prism 1102, can be used to enhance internal reflections as fluorescence emissions pass from the window 1106 to the photosensor 1112.

Figure 12:
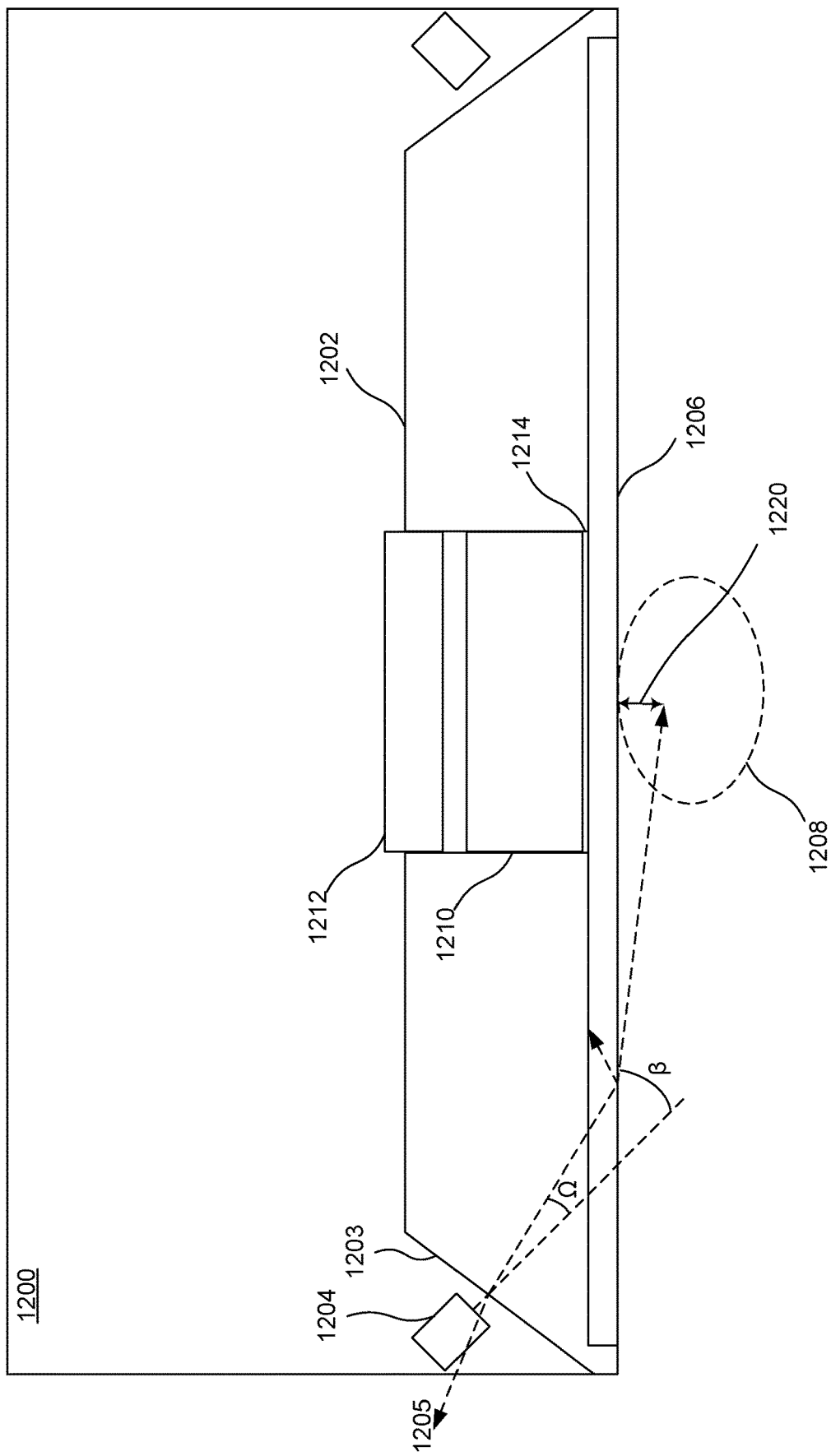
FIG. 12 illustrates an alternate embodiment of an instrument assembly, in accordance with one or more implementations.

FIG. 12 illustrates an instrument assembly 1200, which may be similar or substantially similar to the instrument assembly 800 in FIG. 8. Instrument assembly 1200 comprises a prism 1202, a window 1206, one or more emission sources 1204, a filter assembly 1210, an air gap 1214 formed between the window 1206 and the filter array or assembly 1210, and a photosensor 1212. Further, FIG. 12 also illustrates an analyte workspace 1208 below the window 1206, where the analyte workspace 1208 is a region in the liquid where one or more analytes are being interrogated. As seen in FIG. 12, a larger angle ($\beta$, and hence an analyte workspace 1208 that is closer to the window 1206 may be possible, for instance, when the emission sources 1204 are angled somewhat relative to the angled surfaces 1203 of the prism 1202. For instance, the distance 1220 measured between the window 1206 and an intersection of the emissions (dashed line below window 1206) and a normal to the window 1206 at a center of the photosensor 1212 may be lower than distance 820 seen in FIG. 8. Like distance 820, in some examples, this distance 1220 may be measured from a center of the analyte workspace 1208.

In some embodiments, the angled surface 1203 may be formed such that an angle between a top surface of the prism 1202 and the angled surface 1203 is more vertical (i.e., closer to 90 degrees) than an angle between a top surface of the prism 802 and the angled surface 803 in FIG. 8, for instance. In other words, the angled surface 1203 may be more vertical than it would be when perpendicular to an incident angle of emissions from the emission sources 1204. It should be noted, however, that a portion of the emissions from the emission sources 1204 may be lost to reflection(s) 1205 off the angled surface 1203. In such cases, an anti-reflection coating on the angled surface 1203 may help to reduce such losses.

Figure 13:
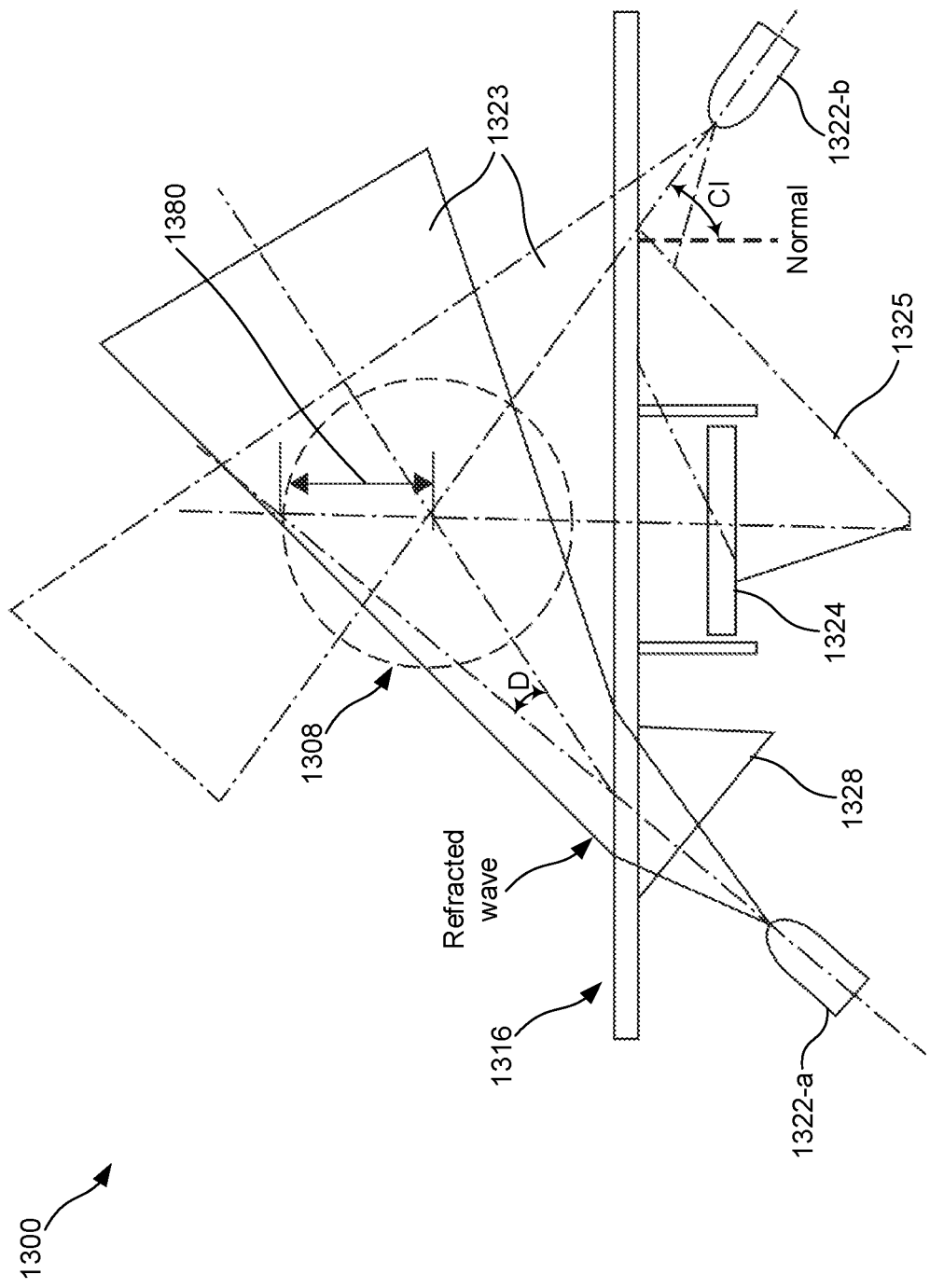
FIG. 13 shows a diagrammatic representation of the light rays using the fluorometers of this disclosure, in accordance with one or more implementations.

FIG. 13 shows a diagrammatic representation 1300 of the light rays using the fluorometers of this disclosure, in accordance with one or more implementations. FIG. 13 shows a prism 1328, a window 1316, one or more emission sources 1322 (e.g., LEDs), an analyte workspace below the window 1316 (above the window in this representation), and a photosensor 1324. In some cases, emissions from the emission sources 1322 may refract towards a line parallel to the window 1316 upon passing through the prism 1328 and intersecting the window-to-liquid interface. For instance, emissions from emission source 1322-a deviate by an angle D after passing through the prism 1328 and the window-to-liquid interface. In this way, the prism 1328 serves to reduce the optical path travelled by the emissions from emission source 1322-a by a distance 1380, which also reduces the distance between the center of the analyte workspace 1308 and the bottom of the window 1316 by the same or a similar distance. FIG. 13 also shows the paths travelled by the exiting beams 1323 that enter the liquid through the window 1316. As shown, exiting beams 1323 originate at the emission sources 1322 and intersect the window 1316 at an angle lower than the critical angle (shown as angle CI with reference to emission source 1322-b). In some cases, the emissions from the emission source 1322-b may reflect back into the instrument assembly of the fluorometer (shown by reflected wave 1325), rather than refract (but still pass through the window-to-liquid interface) if the angle of incidence is greater than the critical angle of incidence CI.

Turning now to FIGS. 14-19 and 21, these figures show an alternative embodiment of a fluorometer. Further, FIG. 20 shows a diagrammatic representation of the light rays for the embodiment shown in FIGS. 14-19 and 21.

Figure 14:
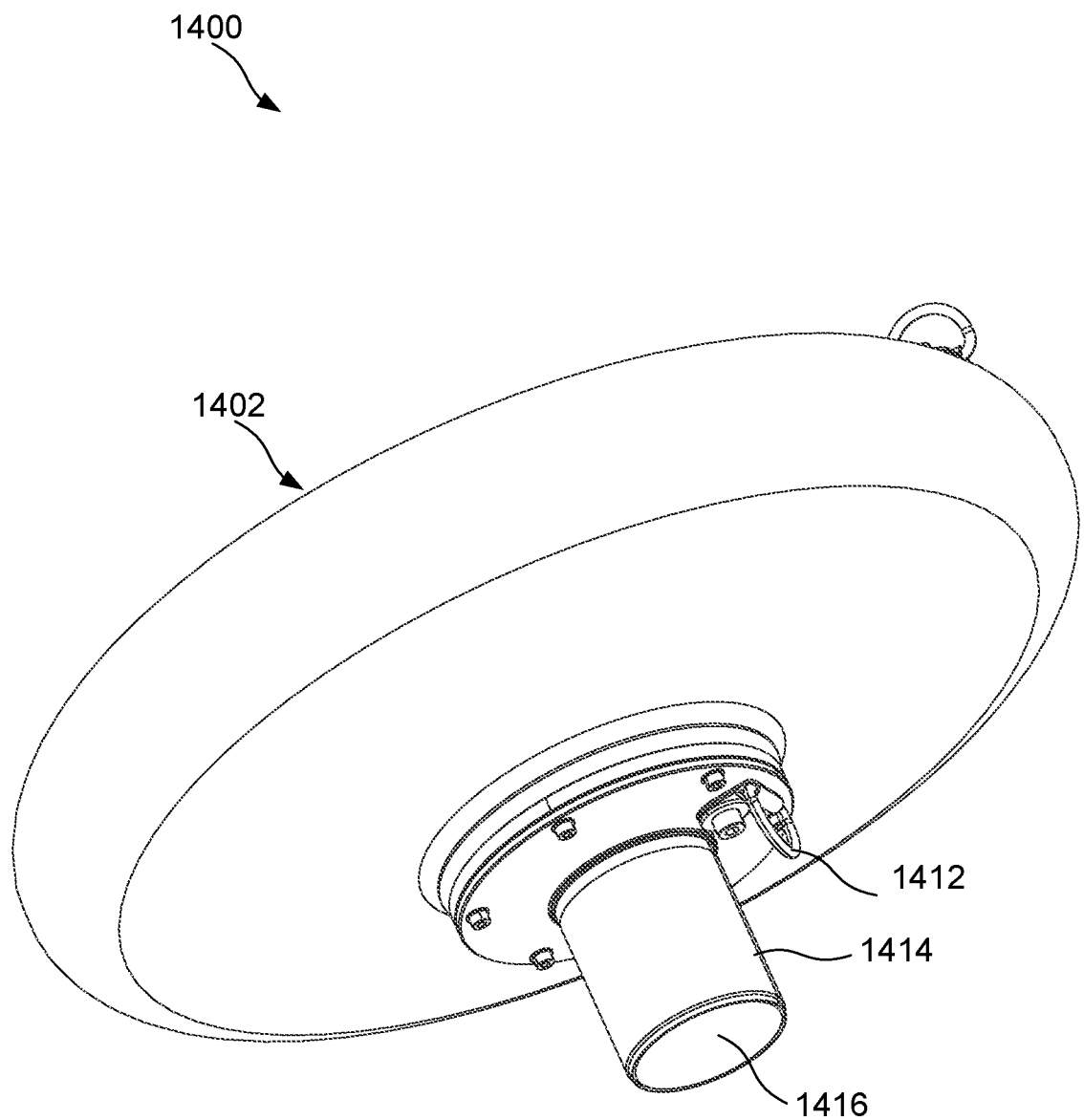
FIG. 14 shows an alternative embodiment of a fluorometer, in accordance with one or more implementations.

FIG. 14 illustrates a fluorometer 1400, according to an alternate embodiment of the disclosure. As seen, fluorometer 1400 comprises a buoy assembly 1402, an instrument assembly described in more detail in the following figures, a window 1416 in the instrument assembly, and an anchoring point 1412 (e.g., a hook or a loop configured to affix to an anchor). In some examples, the buoy assembly 1402, the window 1416, and/or the anchoring point 1412 may be similar or substantially similar to the buoy assembly 102, the window 116, and/or the anchoring point 112 described in relation to FIGS. 1A and 1B. Furthermore, the fluorometer 1400 may also comprise a casing 1414, where the casing 1414 may surround the internal components, such as the prism, photosensor, filter array, emission sources, etc., of the instrument assembly. In some cases, the fluorometer 1400 may further comprise a reflective coating or surface on an inside of the casing, which may serve to confine fluorescence emissions from the analyte workspace below the window 1416 from leaking out and direct them towards the photosensor. In some embodiments, the bottom of the window 1416 may also be coated with one or more anti-reflection layers which may help fluorescence emissions from reflecting back into the liquid, and instead, travel towards to the photosensor. Similar to the fluorometer seen in FIG. 1, the buoy assembly 1402 may comprise a buoyance device and a power structure, where the buoy assembly 1402 is unitary with or coupled to the instrument assembly. In some embodiments, the buoyance device may be a water-tight structure configured to be filled with air. The width or diameter of the buoyance device may greater than its height, which may serve to stabilize the fluorometer in rough water, windy conditions, and/or high-tide. In some cases, the buoy assembly 1402 may further comprise a battery for storing energy from the power structure, where the power structure comprises a solar assembly. Other types of power structures are contemplated in different embodiments. One non-limiting example of a power structure may include a power device capable of harnessing energy from the waves. In some embodiments, the buoy assembly may be coupled to the instrument assembly via a watertight structural connection, the watertight structural connection selected from a group consisting of a flange, a gasket, and a fastener.

Figure 15:
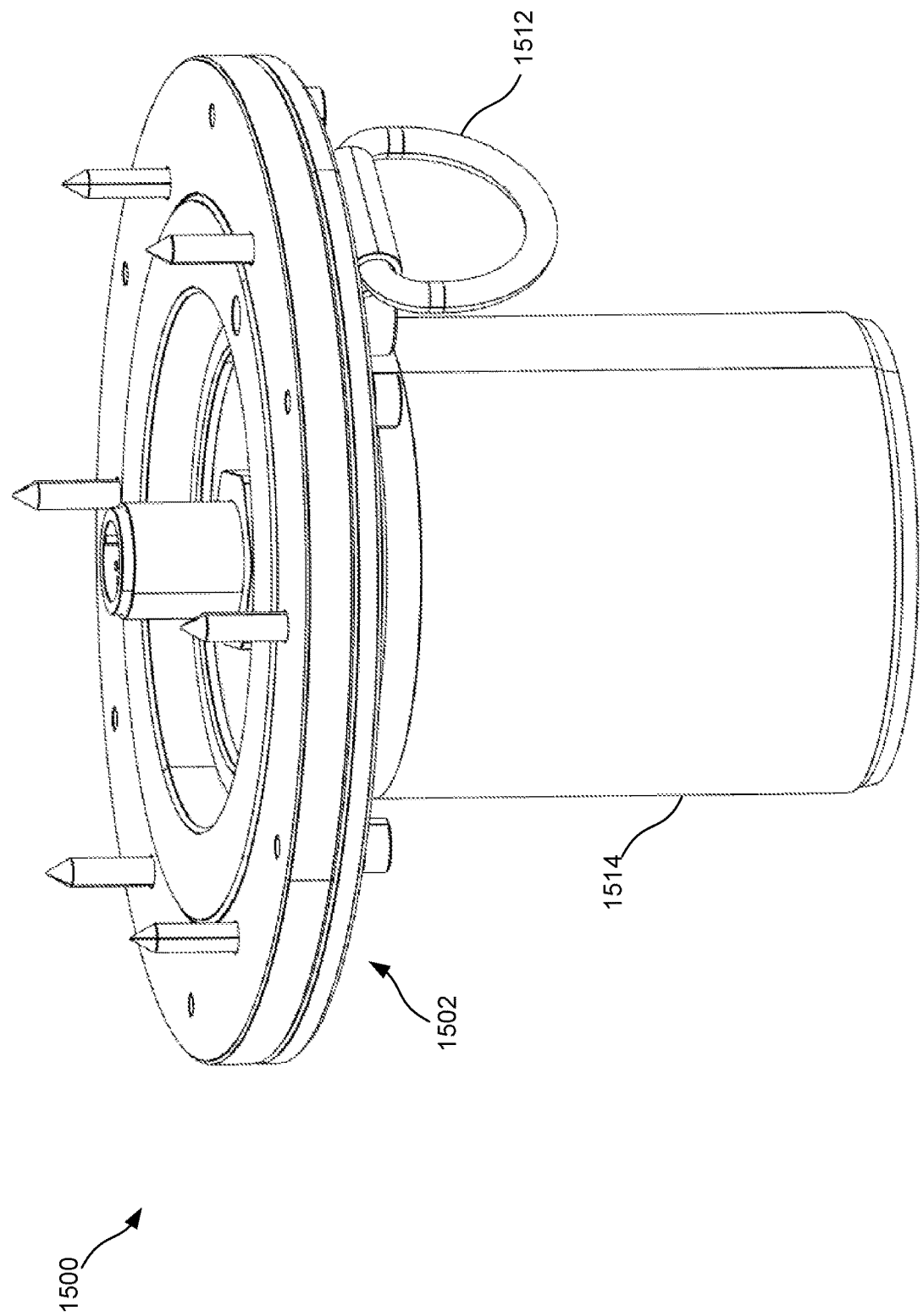
FIG. 15 illustrates a front view of an instrument assembly of the fluorometer in FIG. 14, in accordance with one or more implementations.

FIG. 15 illustrates an instrument assembly 1500 of the fluorometer in FIG. 14. As seen, the instrument assembly 1500 comprising a casing 1514 for housing the internal components of the instrument assembly. Further, the instrument assembly 1500 may be coupled to the buoy assembly (not shown) via a watertight structural connection 1502, the watertight structural connection 1502 selected from a group consisting of a flange, a gasket, and a fastener. In other cases, the buoy assembly and the instrument assembly 1500 may be formed as a single piece with no seams between the two.

Figure 16:
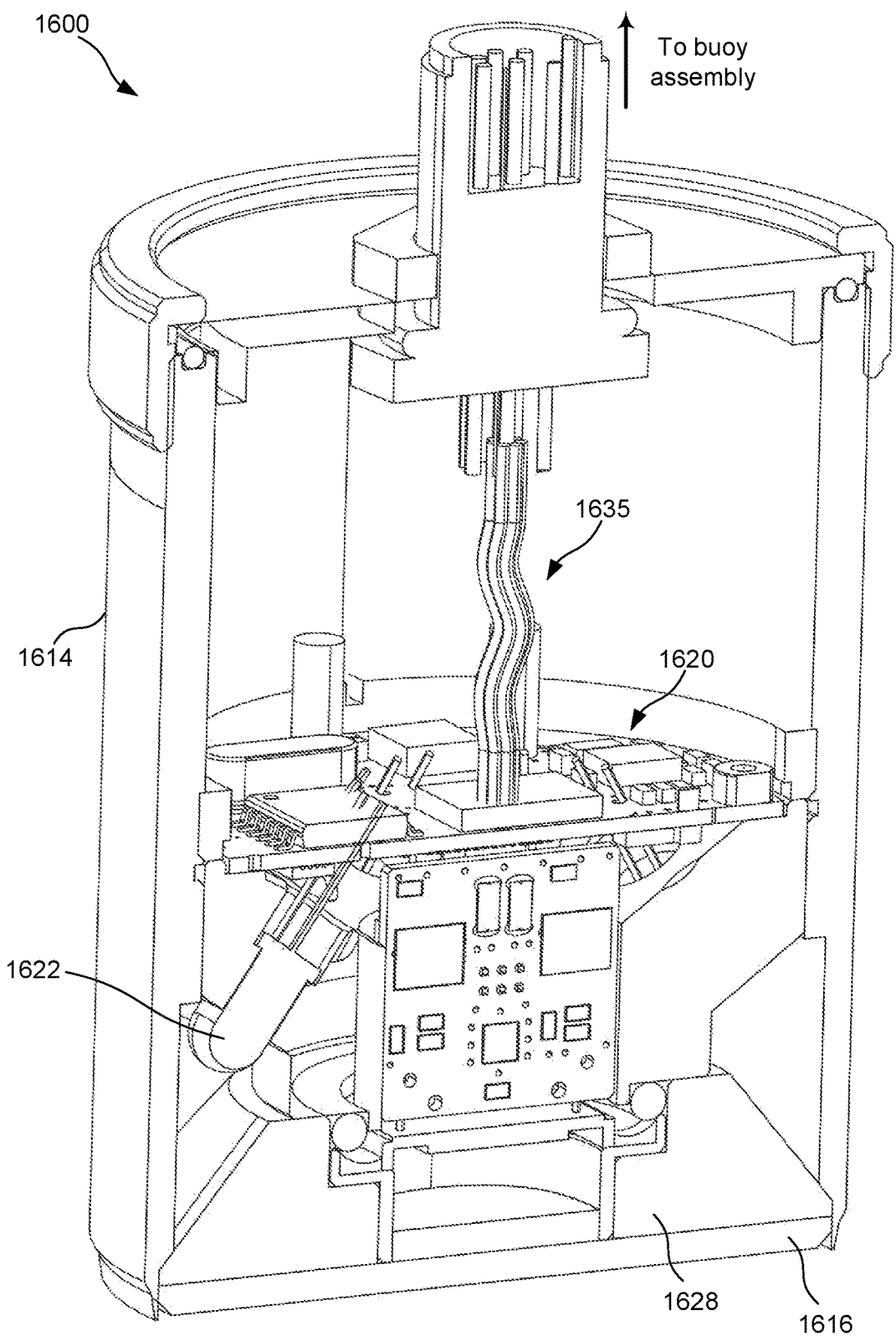
FIG. 16 illustrates a cross section view of the instrument assembly in FIG. 15, in accordance with one or more implementations.

FIG. 16 illustrates a cross-section view of an instrument assembly 1600. The instrument assembly 1600 may implement one or more aspects of the instrument assembly 1500 previously described in relation to FIG. 15. As shown, instrument assembly 1600 comprises a casing 1614, one or more emission sources 1622, a prism 1628, and a window 1616. Additionally, the instrument assembly 1600 may also comprise a circuit assembly 1620 and a cable 1635 coupling the circuit assembly to the buoy assembly, for instance, a power structure and battery in the buoy assembly. In addition to power, in some cases, the cable 1635 may also be configured to carry data to the buoy assembly. In some cases, the buoy assembly may comprise a wireless transmitter (not shown) housed in a waterproof casing or housing, where the wireless transmitter may be configured to transmit information pertaining to the fluorescence emissions detected by the photosensor (not shown) to a remote off-site location. In some embodiments, the circuit assembly 1620 may comprise a fluorescence processor configured to identify one or more analytes in the analyte workspace below the window based on fluorescence information received from the photosensor. In this example, the one or more emission sources 1622 may be angled outward (i.e., away from a central axis of the instrument assembly 1600) unlike the emission sources 322 in FIG. 3 that are angled inward toward the central axis.

Figure 17:
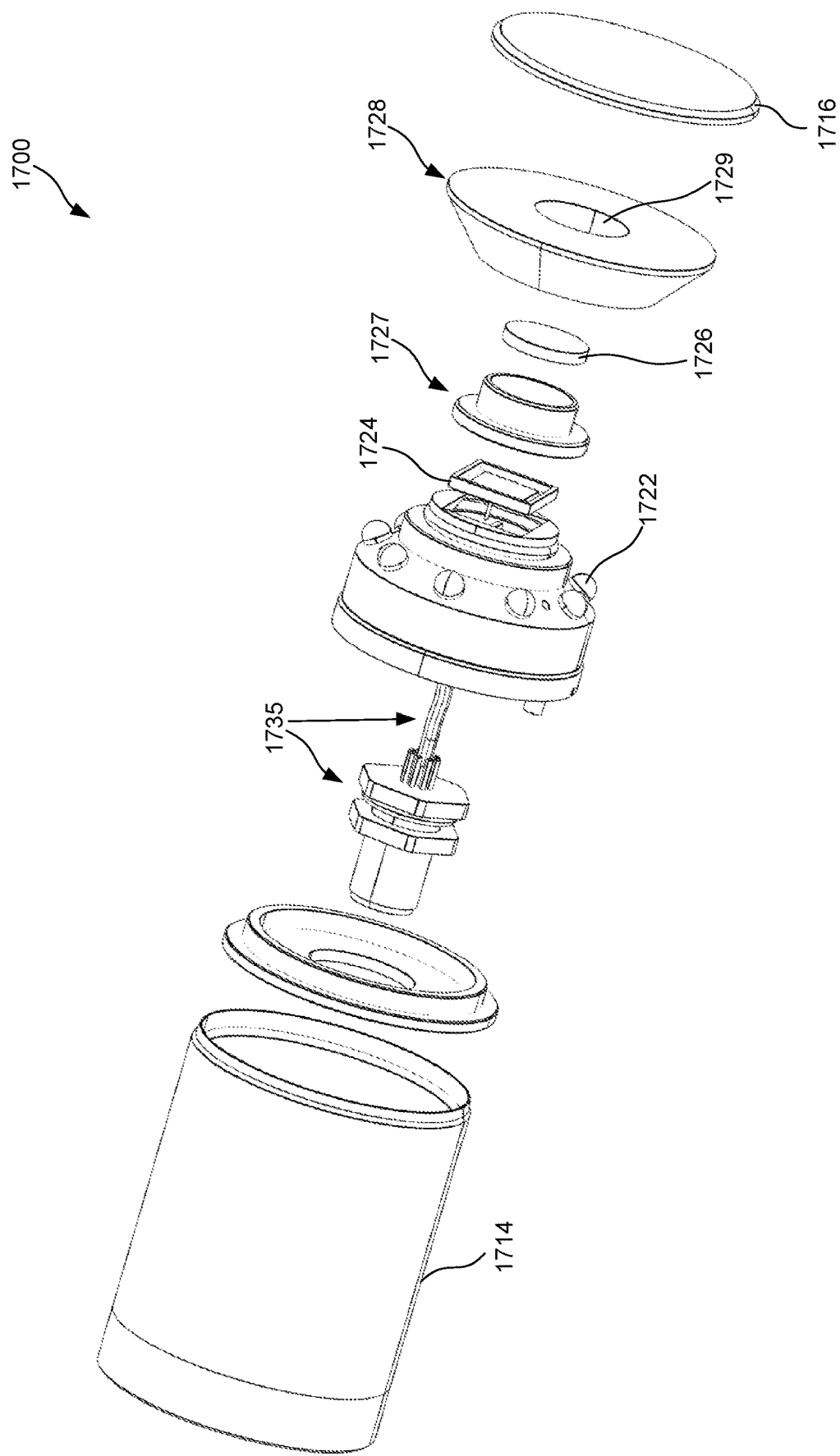
FIG. 17 illustrates an exploded view of the instrument assembly in FIG. 15, in accordance with one or more implementations.

FIG. 17 illustrates an exploded view of an instrument assembly 1700. The instrument assembly 1700 may implement one or more aspects of the instrument assembly 1600 previously described in relation to FIG. 16. As shown, instrument assembly 1700 comprises a casing 1714, one or more emission sources 1722, a prism 1728, and a window 1716. Additionally, the instrument assembly 1700 may also comprise a circuit assembly (shown as circuit assembly 1820 in FIG. 18) and a cable 1735 coupling the circuit assembly to the buoy assembly, for instance, a power structure and battery in the buoy assembly. In addition to power, in some cases, the cable 1735 may also be configured to carry data to the buoy assembly. In some cases, the buoy assembly may comprise a wireless transmitter (not shown) housed in a waterproof casing or housing, where the wireless transmitter may be configured to transmit information pertaining to the fluorescence emissions detected by the photosensor 1724 to a remote off-site location. In some embodiments, the circuit assembly may comprise a fluorescence processor configured to identify one or more analytes in the analyte workspace below the window 1716 based on fluorescence information received from the photosensor 1724. In this example, the one or more emission sources 1722 may be angled outward (i.e., away from a central axis of the instrument assembly 1700) unlike the emission sources 322 in FIG. 3 that are angled inward toward the central axis. In some cases, the one or more emission sources 1722 may be similar or substantially similar to the emission sources 322 in FIG. 3. For instance, the one or more emission sources 1722, which may be LEDs, may be configured to emit light in wavelengths or bands that coincide with an absorption or fluorescence band or peak for an analyte in the liquid (e.g., water) being interrogated. In one example, the emission sources 1722 can include a plurality of LEDs operating at blue frequencies, for instance at or near 490 nm.

As illustrated, the instrument assembly 1700 may also comprise a filter assembly 1726, wherein the filter assembly 326 may be shaped and sized to fit within a filter housing 1727 that can include a reflective inner surface. Alternatively, in lieu of the filter housing 1727, the inner surface of an annular aperture 1729 in the prism 1728 can be reflective. The filter assembly 1726 may be positioned between the window 1716 and the photosensor 1724, and may comprise one or more of a high pass filter, a low pass filter, a band pass filter, or even a band reject filter.

Figure 18:
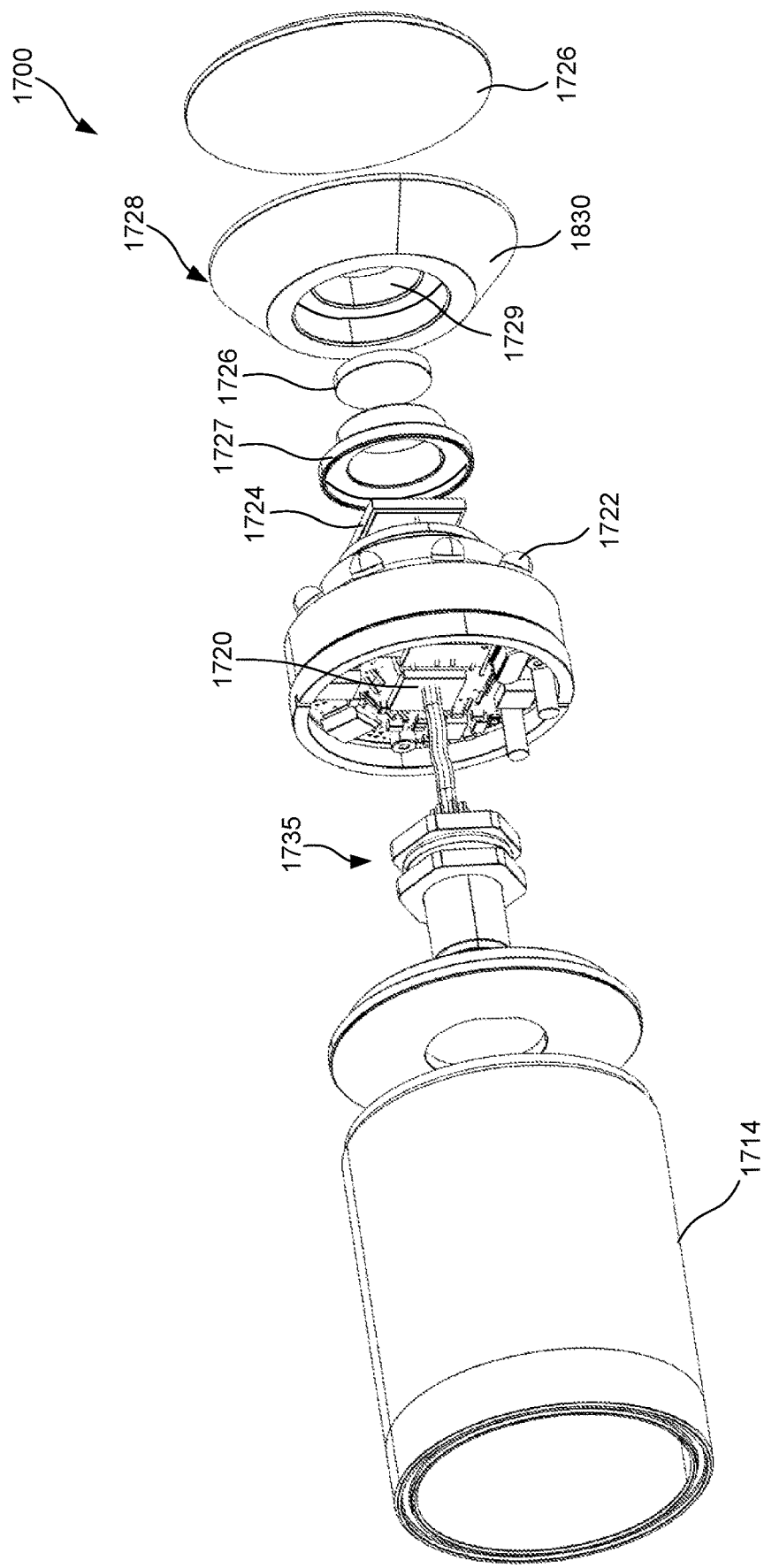
FIG. 18 illustrates another exploded view of the instrument assembly in FIG. 15, in accordance with one or more implementations.

FIG. 18 illustrates another exploded view of the instrument assembly 1700 previously described in relation to FIG. 17. As seen, the prism 1728 comprise one or more angled surfaces 1830, similar to the angled surfaces 330 previously seen and described in relation to FIG. 3. In some cases, the index of refraction of the prism 1728 may be the same or approximately the same as the index of refraction of the window 1716. In some embodiments, the window 1716 and the prism 1728 may be formed of the same material, such as glass, fused silica, sapphire, to name three non-limiting examples. Alternatively, the prism 1728 may be formed using a polycarbonate having a similar index of refraction as the window 1716. In some cases, the angular aperture 1729 of the prism 1728 may comprise a reflective inner surface, which may help direct fluorescence emissions towards the photosensor 1724.

Figure 19:
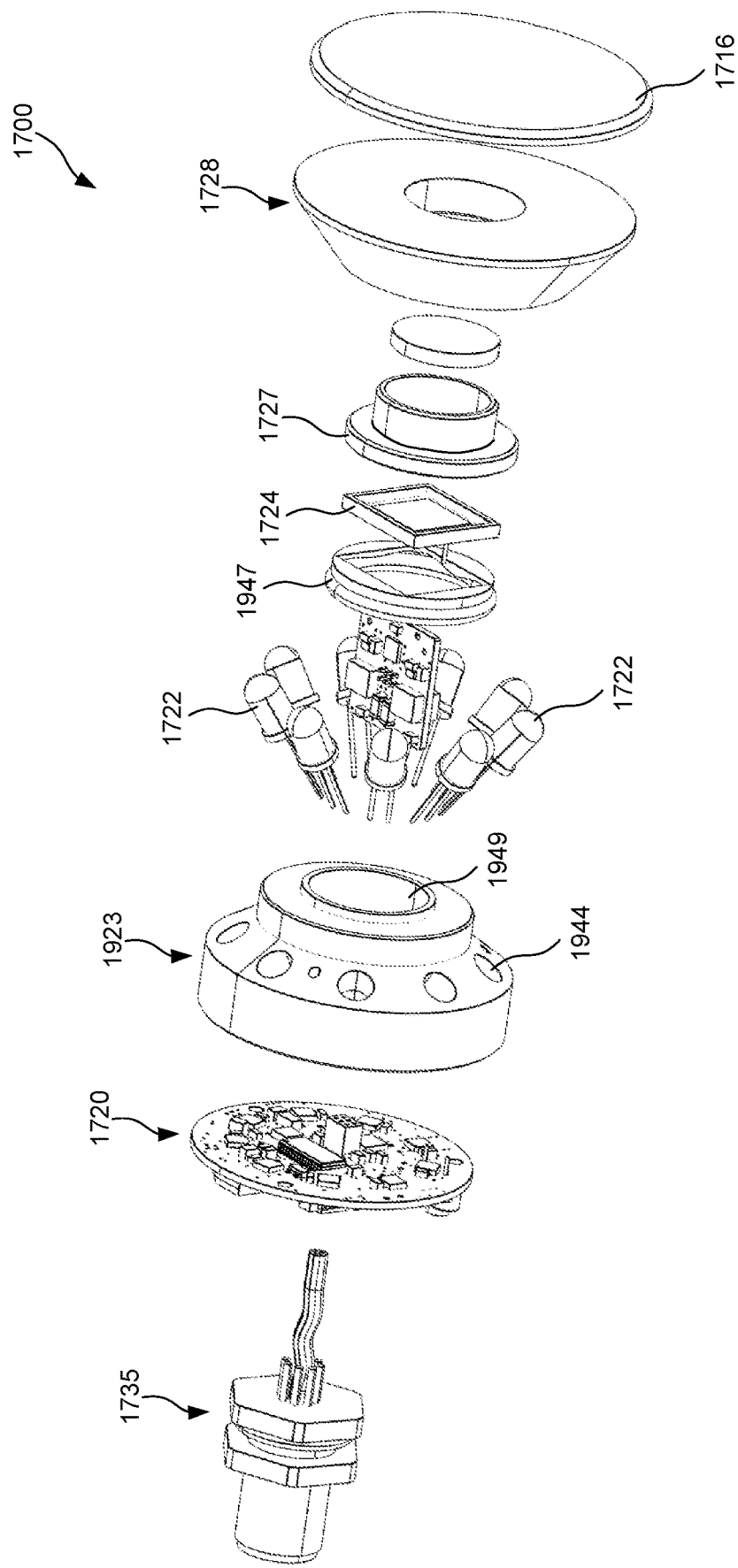
FIG. 19 illustrates another exploded view of the instrument assembly in FIG. 15, in accordance with one or more implementations.
Figure 20:
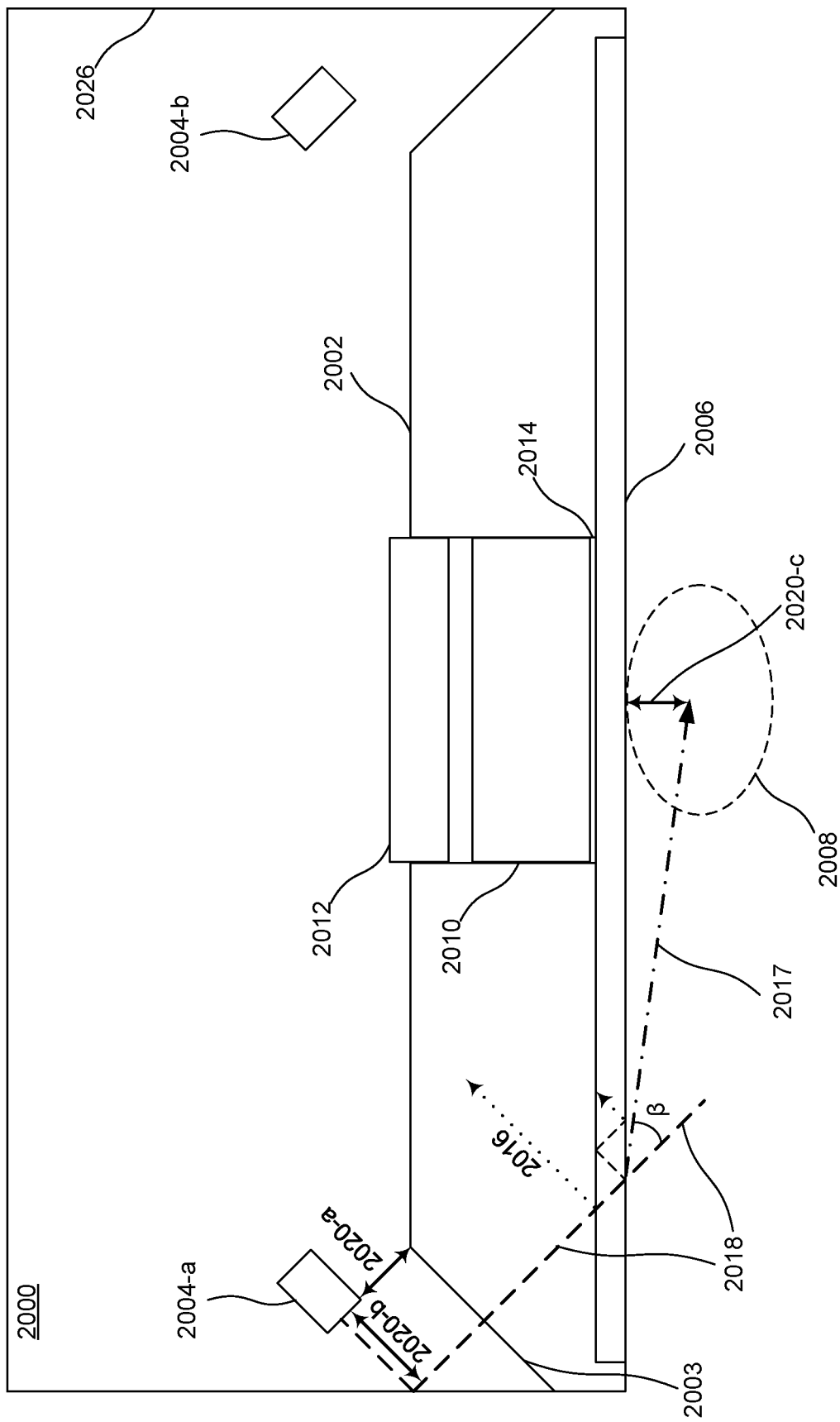
FIG. 20 shows a diagrammatic representation of the light rays for the embodiment shown in FIGS. 14-19, in accordance with one or more implementations.

FIG. 19 illustrates another exploded view of the instrument assembly 1700 in FIG. 17, in accordance with one or more implementations. In this view, details of a housing 1923 in which the emission sources 1722 are arranged are clearly visible. As shown, the housing 1923 may comprise one or more sockets (or indentations) 1944, one for each emission source 1722. Furthermore, the housing 1923 may also comprise an aperture 1949 shaped and sized to provide a snug fit to a frame 1947 in which the photosensor 1724 may be arranged.

Turning now to FIG. 20, an instrument assembly 2000 including a prism 2002, a plurality of emission sources 2004 (e.g., emission source 2004-a, emission source 2004-b), a window 2006, an analyte workspace 2008 below the window 2006, a filter assembly 2010 comprising one or more filters, an air gap 2014 between the window 2006 and the filter assembly 2010, and a photosensor 2012 are shown. The instrument assembly 2000 in FIG. 20 may be an example of the instrument assembly 1600 and/or 1700 previously described in relation to FIGS. 16 and 17-19, respectively. As shown, the emission sources 2004 can be arranged at a distance 2020-a from the prism 2002 and a distance 2020-b from walls 2026 of the instrument assembly 2000, where the walls 2026 may include a reflective coating or material such that some or all emissions from the emission sources 2004 are reflected toward the prism 2002.

FIG. 20 shows that the initial emission 2018 is partially transmitted (e.g., transmission 2017 shown by the dash-dot line) and partially reflected (e.g., reflection 2016 shown by the dotted lines) at the prism-to-window interface. In the prior art, transmission was maximized by orienting the emission sources 2004 at a steep angle, thereby reducing the portion reflected from the prism-window interface. However, such an arrangement also pushed the analyte workspace 2008 deeper in the water and further from the window 2006 and hence from the photosensor 2012. This disclosure uses a prism 2002 arranged in contact with the window 806, where both the prism 2002 and the window 2006 have relatively the same indices of refraction (or the same index of refraction), such that a much shallower or lower angle can be used for the emission sources 2004, while still minimizing the portion of emissions that are reflected and maximizing the transmitted emissions. In some cases, the use of such a structure for the instrument assembly 2000 may achieve distances (i.e., measured as distance 2020-c) of around or less than 1 cm between the analyte workspace 2008 and the bottom of the window 2006. In some examples, this distance 2020-c may be measured from a center of the analyte workspace 2008.

In some cases, as the emission 2018 is reflected off of the reflective surface of wall 2026, it intersects the angled surface 2003 of the prism and travels through the prism 2002 and hits the bottom of the window 2006, or the window-to-liquid interface. As shown, the emission 2018 tends to bend inward toward the analyte workspace 2008. In some cases, this bending may be enhanced by the shallower angle of the reflected emission 2018 relative to the window 2006. While there is little if any bending at the prism-to-window interface, due to the similarity (or equivalence) of the indices of refraction and lack of air gap therebetween, emission 2018 may nonetheless depart from this initial path of incidence by an angle β after passing into the liquid (i.e., due to the liquid having a different index of refraction than the prism and/or window).

In some circumstances, some reflections 2016 off the bottom of the window 806, or the window-to-liquid interface, may return to the prism 2002, bounce around one or more times within the window 2006 as a byproduct of TIR, or bounce around and then exit into the liquid. In some circumstances, some of these reflections 2016 can enter the filter assembly 2010. To mitigate this, the filter assembly 2010 may be positioned such that there is an air gap 2014 between the filter assembly 2010 and the window 2006, and this air gap may help keep the bouncing reflections 2016 within the window 2006 (i.e., since any interface with a substantial change in index of refraction, for instance, from glass to air, is more likely to cause reflection than transmission). In some cases, a portion of these TIR reflections 2016 may reach ends of the window 2006 and subsequently return toward the middle (e.g., above the analyte workspace) after reflecting off of the ends. In an embodiment, the ends of the window 2006 may be painted or coated with a light-absorbing material (e.g., vantablack or flock paper, to name two non-limiting examples) or a black paint/pigment. Additionally or alternatively, the ends of the window 2006 may be textured, sandblasted, or otherwise roughed up to further enhance the leaking of light out the ends of the window 2006 rather than causing it to reflect back toward the middle. In some other cases, the sides of the filter assembly 2010 and/or sides of the prism 2002 (i.e., where the prism 2002 meets the filter assembly 2010) may include a reflective surface or housing to help light (i.e., the fluorescent emissions) passing through the filter assembly 2010 to reflect and arrive at the photosensor 2012. In other words, the reflective surface on the sides of the filter assembly 2010 and/or the prism 2002 may serve to confine light (i.e., the fluorescent emissions) above the window and direct it towards to the photosensor 2012.

In some circumstances, the window-to-liquid interface may experience the greatest losses to reflections since the difference in the index of refraction is larger than, for instance, at the prism-to-window interface. In some embodiments, a bottom of the window 2006 may also be coated, for instance, with an anti-reflection coating or anti-reflection layers, which may help reduce reflections within the window 2006 and encourage transmission into the liquid.

Figure 21:
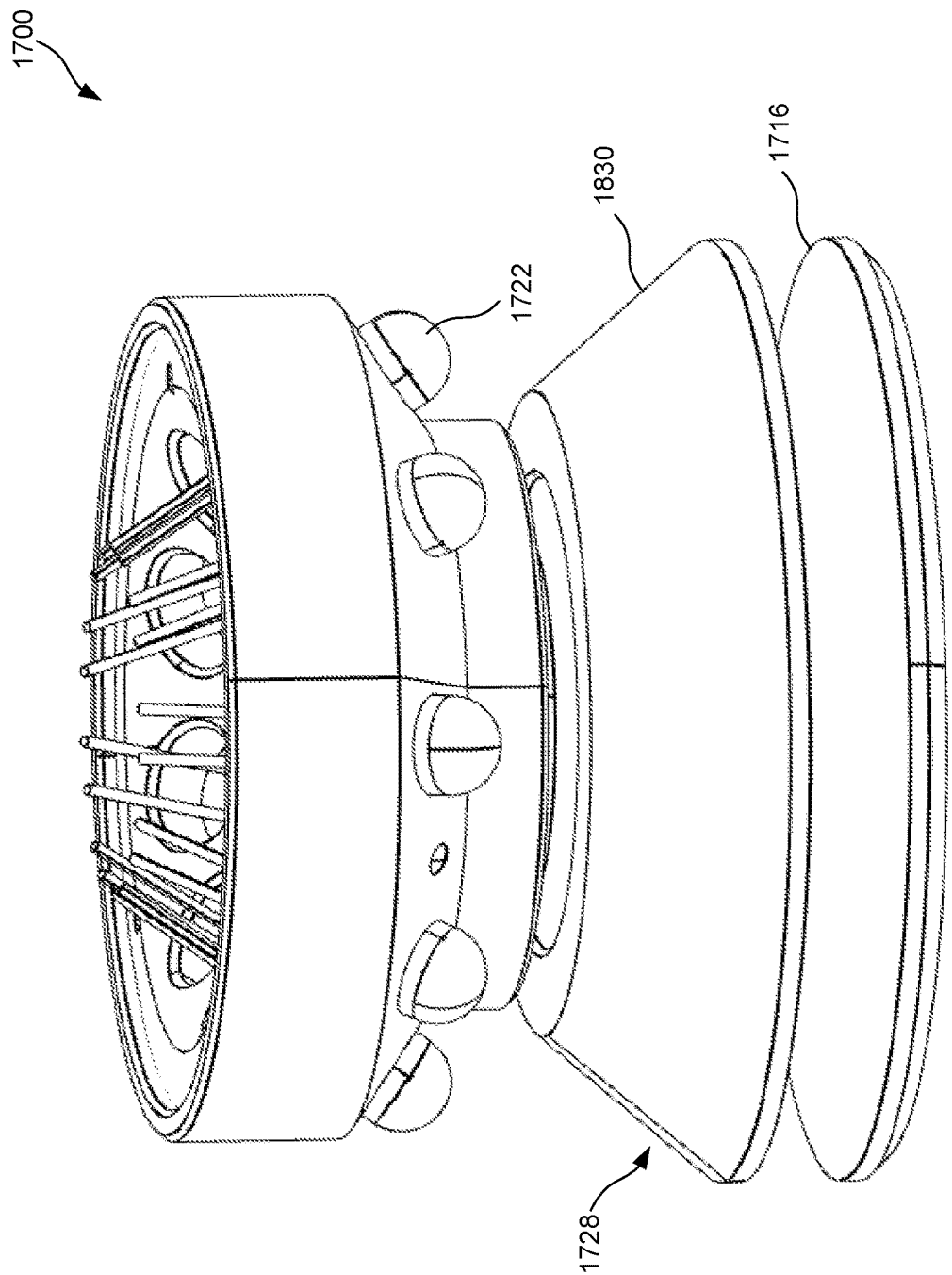
FIG. 21 illustrates a front view of the prism assembly, window, and emission sources of the instrument assembly in FIG. 17, in accordance with one or more implementations.

FIG. 21 illustrates a front view of the instrument assembly 1700 in FIGS. 17 and 18 depicting the one or more emission sources 1722, prism 1728 having one or more angled surfaces 1830, and a window 1716.

Figure 22:
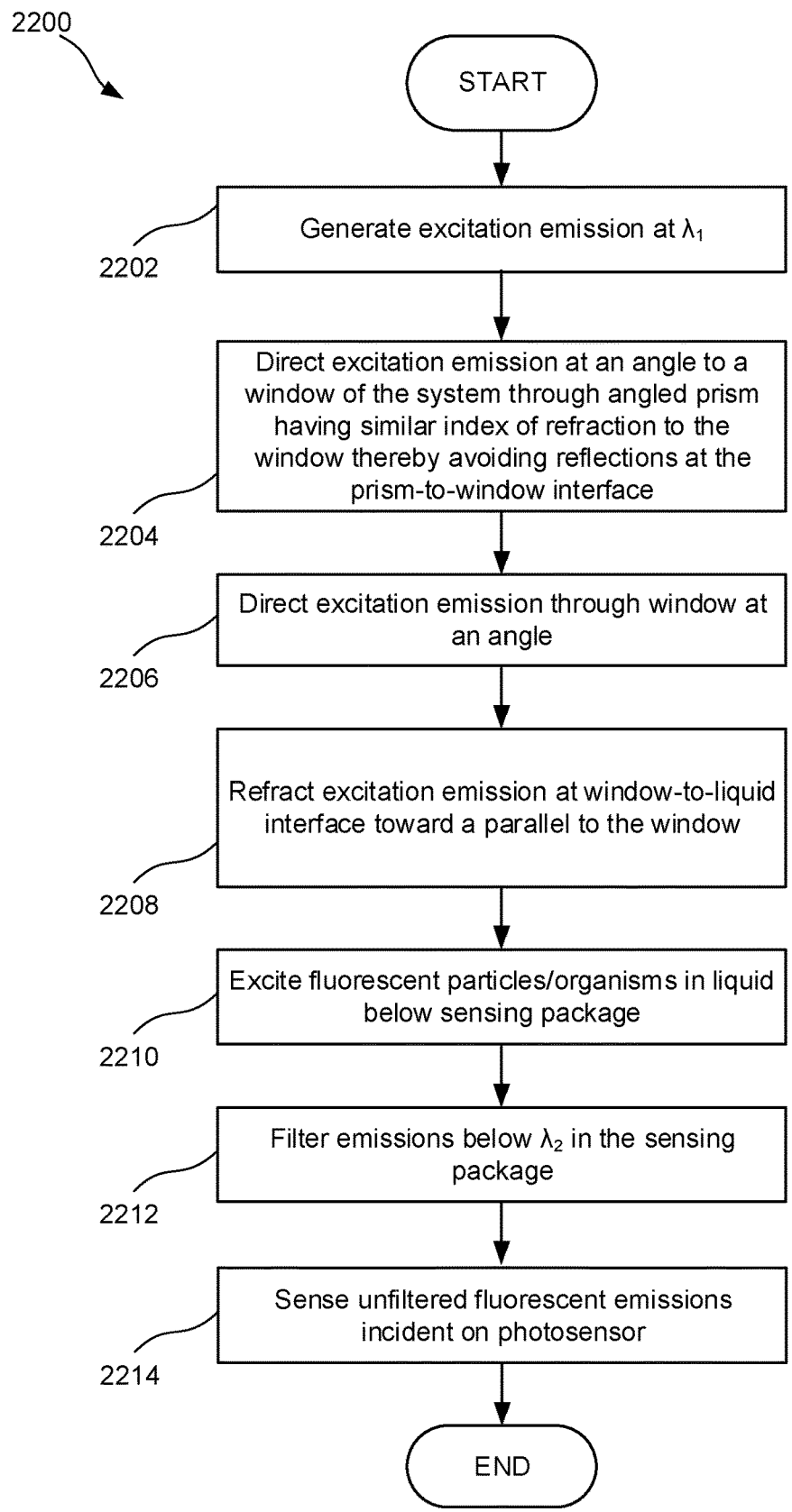
FIG. 22 illustrates a method for utilizing a fluorometer, according to an embodiment of this disclosure.

FIG. 22 illustrates a method 2200 for utilizing the fluorometers disclosed in this application, in accordance with one or more implementations. As shown, the method 2200 may comprise generating 2202 an excitation emission at a first wavelength ($\lambda_1$), where the first wavelength may be selected to coincide with an absorption or fluorescence band of at least analyte to be interrogated in an analyte workspace in a liquid (e.g., water). In some cases, the excitation emission may be generated via the use of at least one emission source, such as an LED.

In some cases, the method may further comprise directing 2204 the excitation emission at an angle to a window of an instrument assembly of the fluorometer, for instance, via an angled prism having a similar index of refraction as the window, which may serve to avoid or minimize reflections at the prism-to-window interface. In some cases, an angled prism may refer to a prism having one or more angled surfaces, such as prism 328 in FIG. 3, or prism 1728 in FIGS. 17 and 18.

The method 2200 may further include directing 2206 the excitation emission through the window at an angle.

In some cases, the method 2200 may include refracting 2208 the excitation emission at the window-to-liquid interface towards a parallel to the window. In some embodiments, the index of refraction of the window may be selected such that emissions intersecting the window are bent inward towards the analyte workspace below the window. In some cases, a distance between an intersection of the emissions and a line passing through the center of the analyte workspace may be at or near 1 cm, although smaller distances are contemplated in different embodiments. In some aspects, by refracting the excitation emission towards a parallel to the window, the distance between the analyte workspace at the bottom of the window may be minimized, which may enhance fluorescent emission detection at the photosensor.

In some cases, the method 2200 may then include exciting 2210 fluorescent particles and/or organisms (i.e., analytes) in the liquid below the sensing package. Next, the method 2200 may comprise filtering 2212 emissions below a threshold wavelength ($\lambda 2$) in the sensing package. The filtering 2212 may be performed by one or more filters of a filter array or assembly, such as filter assembly 326 in FIG. 3 or filter assembly 1726 in FIG. 17. In some cases, the filter array or assembly may comprise a high pass filter, a band pass filter, a low pass filter, or even a band reject filter. In this way, only emissions of a particular wavelength or band of wavelengths may arrive at the photosensor. For instance, if algae fluoresces at 650 nm, emissions having a wavelength below 620 nm may be filtered out, which may serve to optimize processing of the fluorescent emissions.

In some cases, after filtering 2212 the emissions below a certain threshold wavelength, the method 2200 may comprise sensing 2214 unfiltered fluorescent emissions incident on the photosensor. In some cases, the instrument assembly may comprise a fluorescence processor configured to identify one or more analytes based on the fluorescence information received from the photosensor, where the fluorescence information may comprise at least a wavelength or frequency and a magnitude of fluorescence peaks. In some embodiments, the fluorescence processor may be configured to identify the one or more analytes based on correlating the fluorescence information to known fluorescent signatures of algal blooms, for instance.

Figure 23:
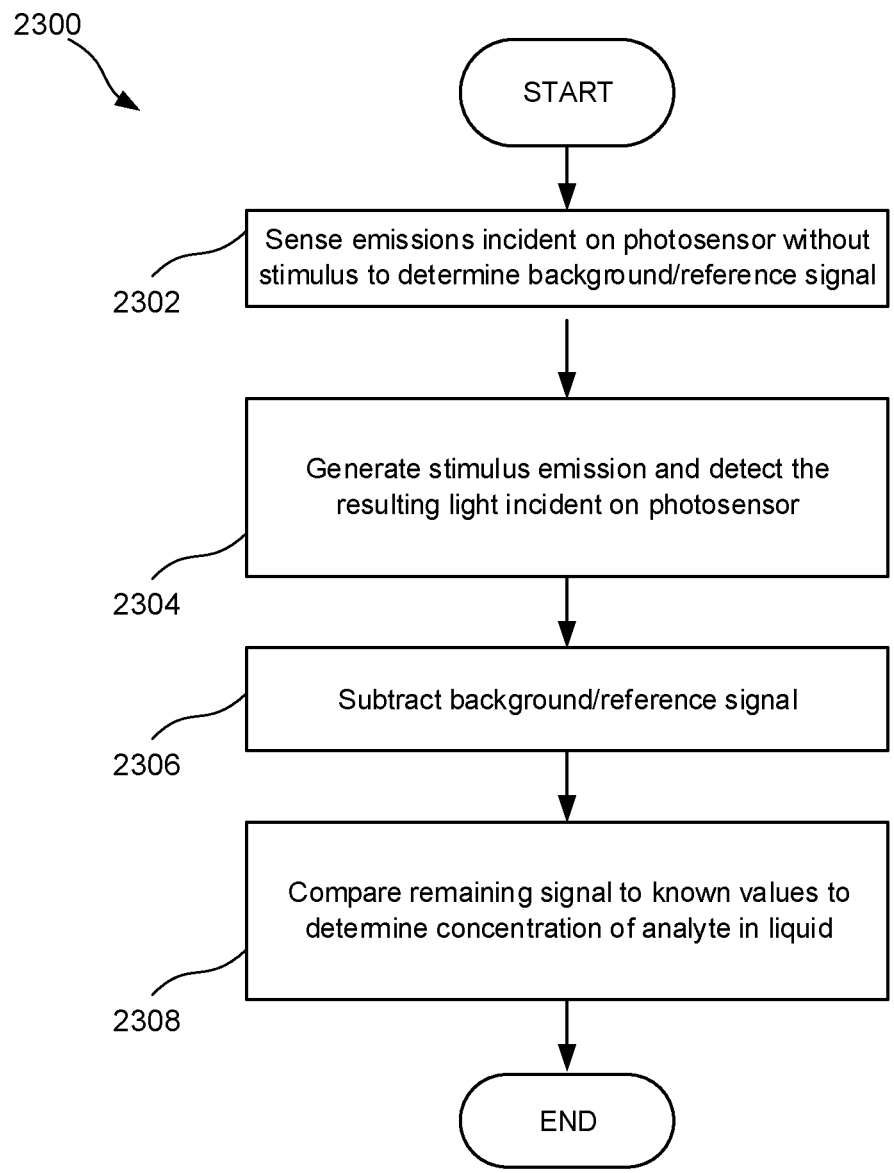
FIG. 23 illustrates a method for utilizing a fluorometer, according to an alternate embodiment of this disclosure.

FIG. 23 illustrates an embodiment of a method 2300 for utilizing the fluorometers disclosed in this application. FIG. 23 implements one or more aspects of the figures described herein.

In some cases, method 2300 comprises sensing 2302 emissions incident on a photosensor within an instrument assembly to determine a background or reference signal. Next, the method 2300 comprises generating 2304 stimulus emissions and detecting the resulting light or emissions incident on the photosensor. In this way, the background or reference signal may be subtracted 2306. Further, the method 2300 may comprise comparing 2308 the remaining signal (i.e., after subtraction) to known values, for instance, from a lookup table, to determine a concentration of one or more analytes in the liquid.

In some cases, method 2300 may be implemented by the fluorescence processor or another processor in electronic communication with the photosensor. Further, the method 2300 may be carried out via a processor receiving computer readable instructions from one or more tangible programmable computer readable media. In some cases, the computer readable media may be arranged on the processors or on the same system-on-chip as the processor. In some examples, the processor, such as the fluorescence processor, may receive data from and provide data and instructions to other portions of the system or instrument assembly, such as from the photosensor and/or the LEDs. For instance, the processor may be configured to control when the LEDs turn on/off, and receive fluorescence information from the photosensor for further processing.

FIGS. 24-32 show yet another alternative embodiment of a fluorometer.

FIG. 24 illustrates a fluorometer 2400, according to an alternate embodiment of the disclosure. As seen, fluorometer 2400 comprises a buoy assembly 2402, an instrument assembly described in more detail in the following figures, a window 2416 in the instrument assembly, and a wiper 2450 for the glass forming the window 2416. In some examples, the buoy assembly 2402 and/or the window 2416 may be similar or substantially similar to the buoy assembly 102 and/or the window 116 previously described in relation to FIGS. 1A and 1B. Furthermore, the fluorometer 2400 may also comprise a casing 2414, where the casing 2414 may surround the internal components, such as the prism, photosensor, filter array, emission sources, etc., of the instrument assembly. In some cases, the fluorometer 2400 may further comprise a reflective coating or surface on an inside of the casing, which may serve to confine fluorescence emissions from the analyte workspace below the window 2416 from leaking out. In this way, the reflective coating may help direct the fluorescent emissions towards the photosensor above the window, prism, and/or filter assembly. In some embodiments, the bottom of the window 2416 may also be coated with one or more anti-reflection layers which may help fluorescence emissions from reflecting back into the liquid, and instead, travel towards to the photosensor. Similar to the fluorometer seen in FIG. 1, the buoy assembly 2402 may comprise a buoyance device and a power structure, where the buoy assembly 2402 is unitary with or coupled to the instrument assembly. In some embodiments, the buoyance device may be a watertight structure configured to be filled with air. The width or diameter of the buoyance device may be greater than its height, which may serve to stabilize the fluorometer in rough water, windy conditions, and/or during high-tide. In some cases, the buoy assembly 2402 may further comprise a battery for storing energy from the power structure, where the power structure comprises a solar assembly. Other types of power structures are contemplated in different embodiments. One non-limiting example of a power structure may include a power device capable of harnessing energy from the waves. In some embodiments, the buoy assembly may be coupled to the instrument assembly via a watertight structural connection, the watertight structural connection selected from a group consisting of a flange, a gasket, and a fastener.

Figure 25:
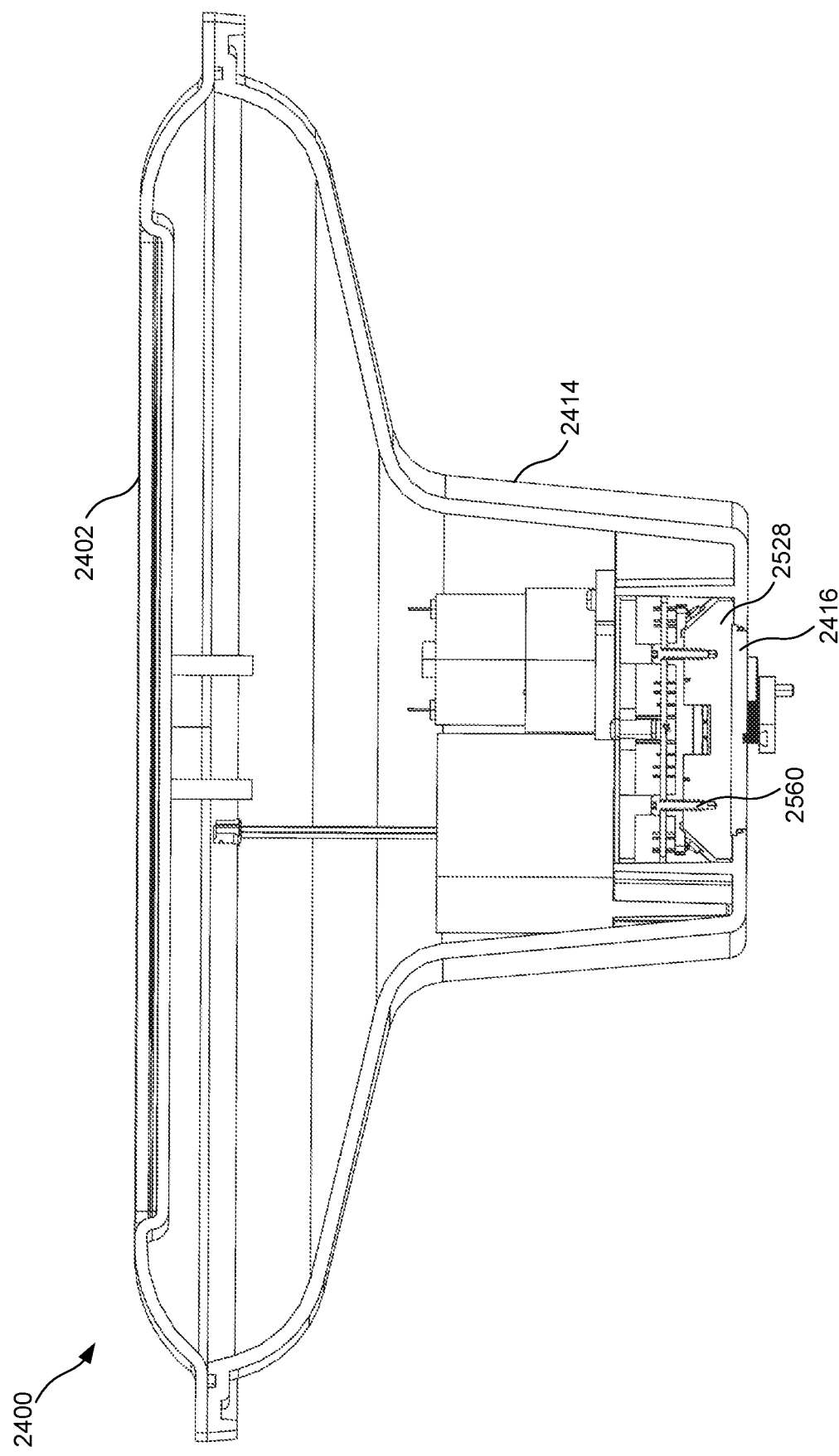
FIG. 25 shows a cross section view of the fluorometer in FIG. 24, in accordance with one or more implementations.

FIG. 25 illustrates a cross section view of the fluorometer 2400 comprising the buoy assembly 2402, the casing 2414, a prism 2528, the window 2416, and one or more fasteners 2560 for securing the prism 2528 within the instrument assembly. In some cases, the prism 2528 may be similar or substantially similar to the prism 328 and/or prism 1728 described above.

Figure 26:
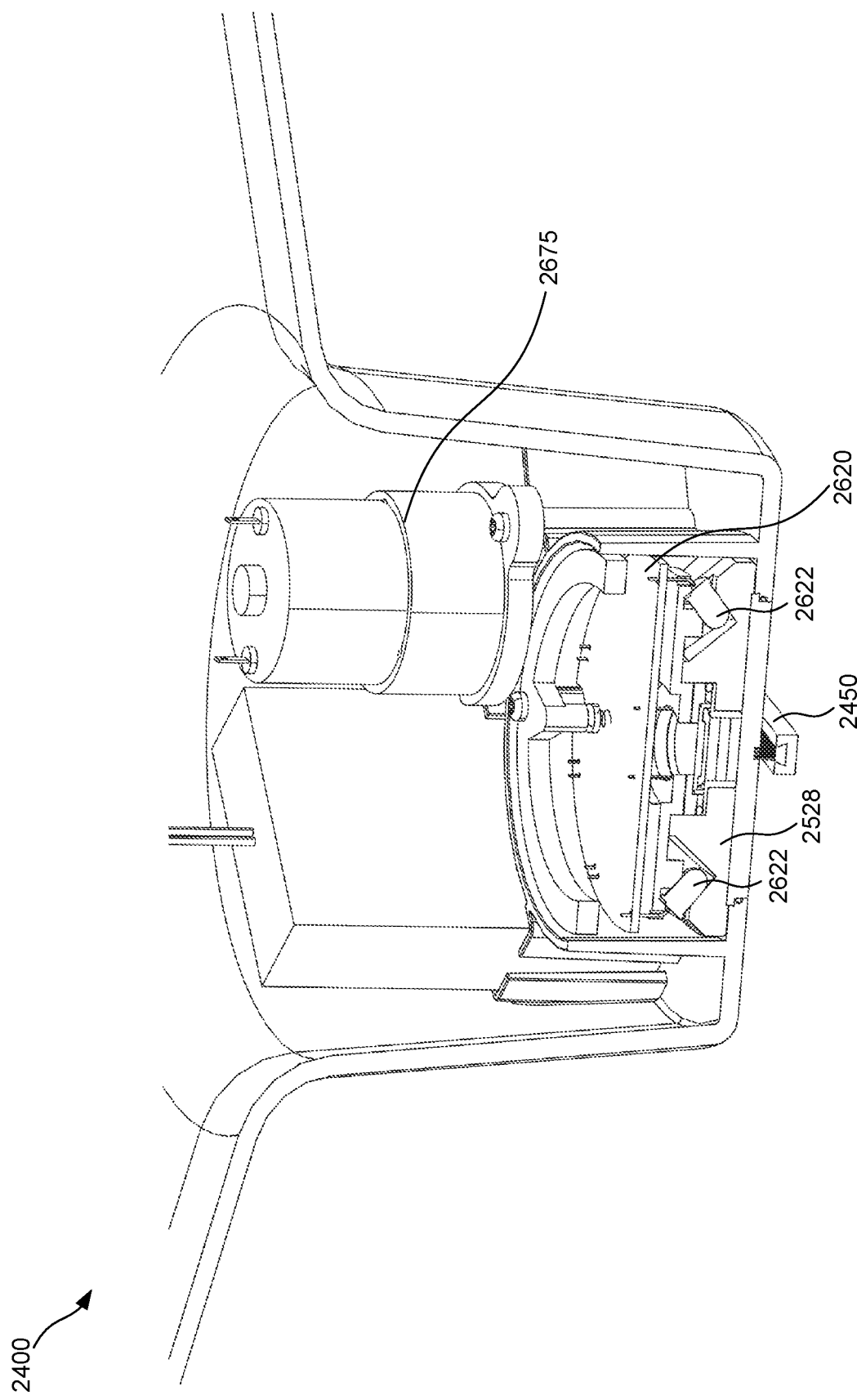
FIG. 26 shows a detailed perspective view of FIG. 25, in accordance with one or more implementations.

FIG. 26 illustrates a close up view of the cross section of the fluorometer 2400 in FIG. 25. Additional details not seen in FIG. 25 are visible, including a circuit assembly 2620 (also referred to as a circuit board), a motor 2675 configured to control the wiper 2450, and one or more emission sources 2622. In this example, the one or emission sources 2622, which may be LEDs, are angled inward towards a central axis of the instrument assembly of the fluorometer 2400. Further, the one or more emission sources 2622 are arranged at or near the prism 2528. In other cases, the emission sources 2622 may be embedded in the prism 2528. In some cases, the circuit assembly 2620 may also be configured to control the motor, for instance, a start/stop of the motor, duration for which motor should be run, etc.

Figure 27:
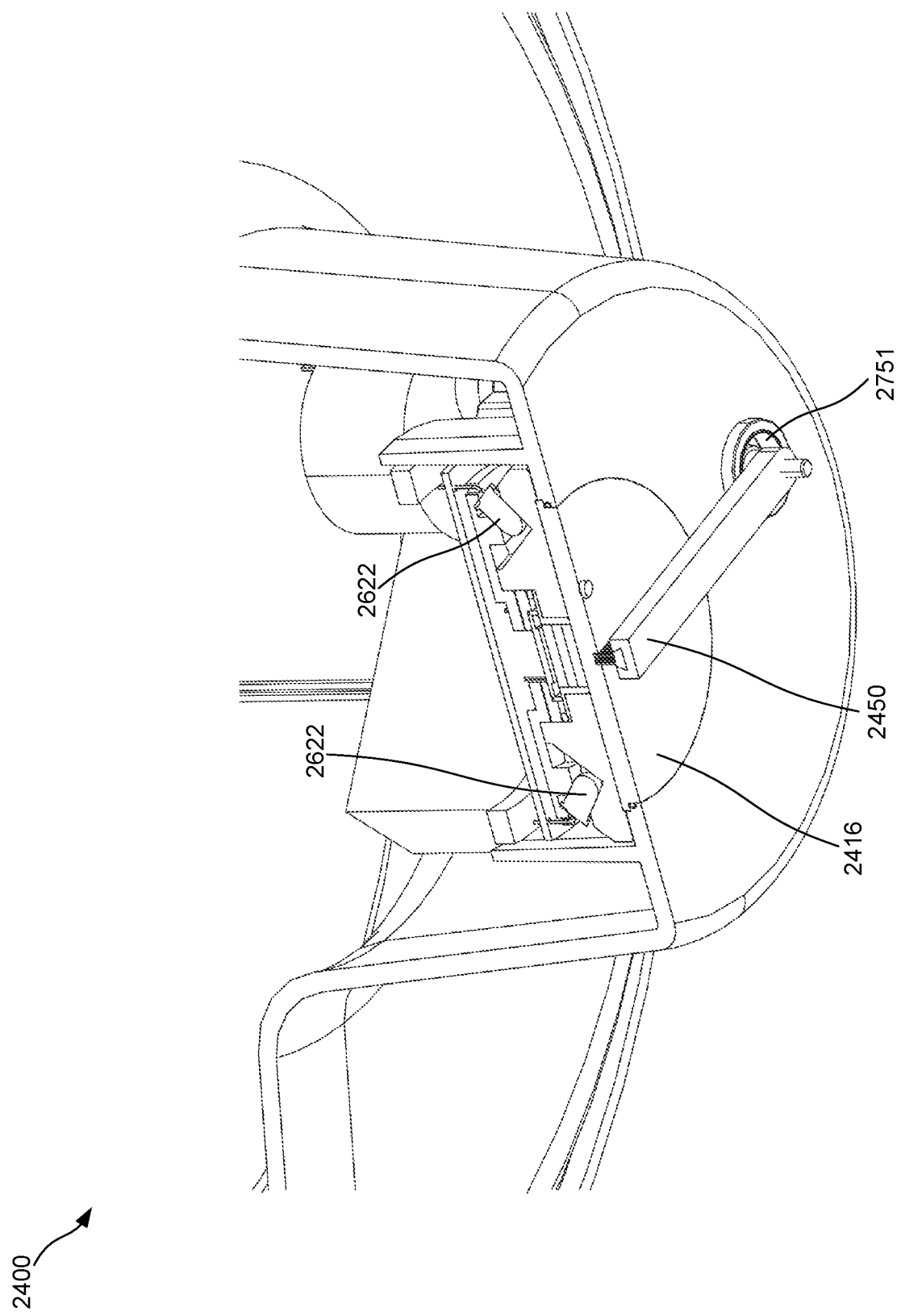
FIG. 27 shows another detailed view of FIG. 25, in accordance with one or more implementations.

FIG. 27 illustrates a bottom cross section view of the fluorometer 2400 showing the wiper 2450 for the window 2416 in greater detail. In some cases, the wiper 2450 may be configured to rotate about a pivot 2751. The wiper 2450 may facilitate in keeping the window 2416 clear and free of mud or other debris, insects, algae, etc., floating in the liquid, which may enhance the quality of fluorescent emission detection at the photosensor in the instrument assembly.

Figure 28:
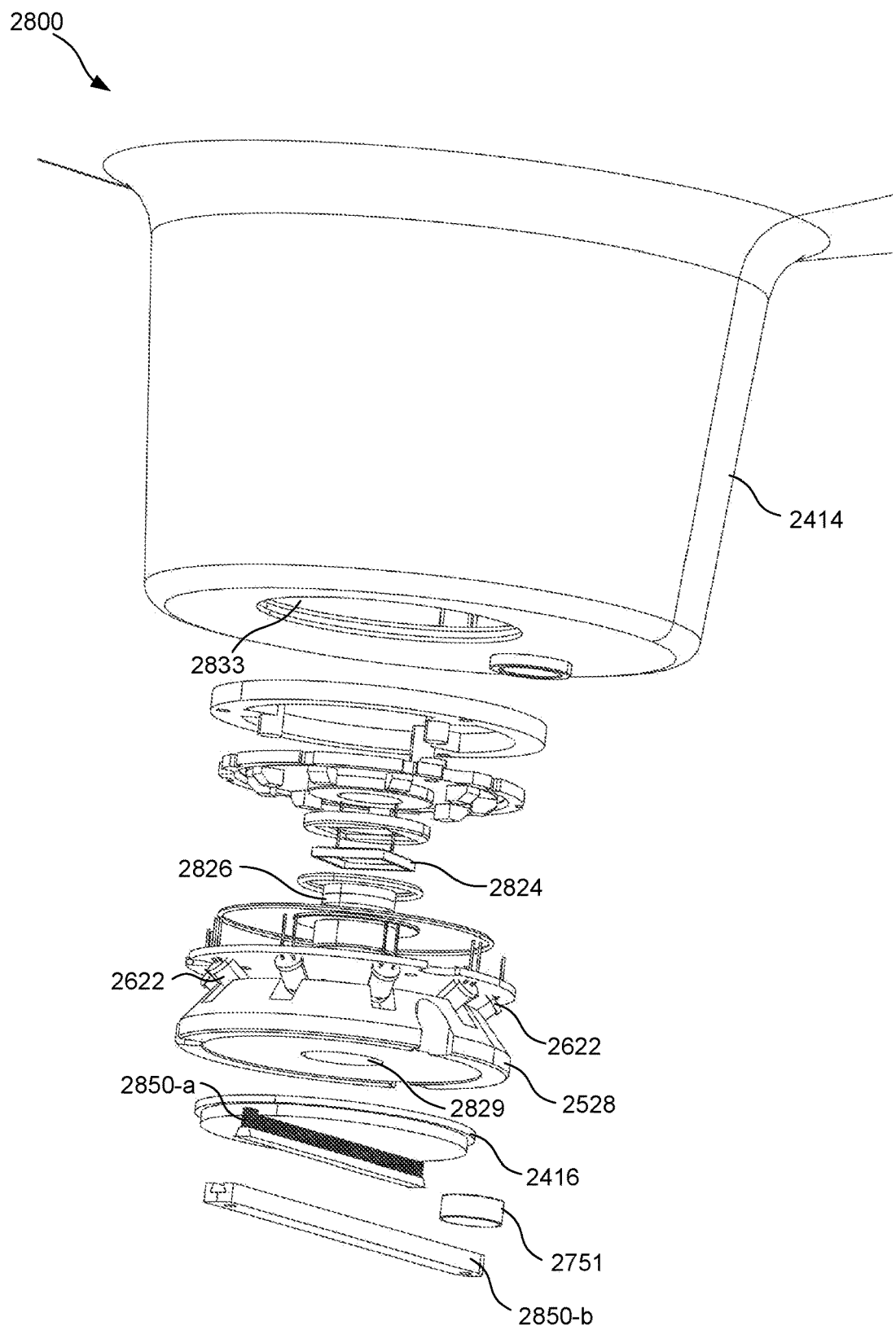
FIG. 28 shows an exploded view of the fluorometer in FIG. 24, in accordance with one or more implementations.

FIG. 28 illustrates an exploded view of an instrument assembly 2800 of the fluorometer seen in FIG. 24. Instrument assembly 2800 may be similar or substantially similar to the instrument assemblies described above, including at least instrument assembly 300 in FIG. 3 and instrument assembly 1700 in FIG. 17. As shown, instrument assembly 2800 comprises a casing 2414, one or more emission sources 2622, a prism 2528, and a window 2416. Additionally, the instrument assembly 2800 may also comprise a circuit assembly (shown as circuit assembly 2620 in FIG. 26) and a cable coupling the circuit assembly to the buoy assembly, for instance, a power structure and battery in the buoy assembly. In addition to power, in some cases, the cable may also be configured to carry data to the buoy assembly. In some cases, the buoy assembly may comprise a wireless transmitter (not shown) housed in a waterproof casing or housing, where the wireless transmitter may be configured to transmit information pertaining to the fluorescence emissions detected by a photosensor 2824 to a remote off-site location. In some embodiments, the circuit assembly may comprise a fluorescence processor configured to identify one or more analytes in the analyte workspace below the window 2416 based on fluorescence information received from the photosensor 2824. In this example, the one or more emission sources 2622 may be angled inward toward the central axis of the instrument assembly. In some cases, the one or more emission sources 2622 may be similar or substantially similar to the emission sources 322 in FIG. 3. For instance, the one or more emission sources 2622, which may be LEDs, may be configured to emit light in wavelengths or bands that coincide with an absorption or fluorescence band or peak for an analyte in the liquid (e.g., water) being interrogated. In one example, the emission sources 2622 can include a plurality of LEDs operating at blue frequencies, for instance at or near 490 nm.

As illustrated, the instrument assembly 2800 may also comprise a filter assembly 2826, wherein the filter assembly 2826 may be shaped and sized to fit within a filter housing (not shown) that can include a reflective inner surface. Alternatively, in lieu of the filter housing, the inner surface of an annular aperture 2829 in the prism 2828 can be reflective. The filter assembly 2826 may be positioned between the window 2416 and the photosensor 2824, and may comprise one or more of a high pass filter, a low pass filter, a band pass filter, or even a band reject filter.

Instrument assembly 2800 also illustrates the individual components of a wiper 2850 (i.e., similar to wiper 2450 in FIG. 24), including a wiper blade 2850-*a* and a frame 2850 for supporting the wiper blade 2850-*a*. In some examples, the wiper 2850 may be configured to be rotatable about pivot 2751 on the lower face of the casing 2414. Further, the wiper 2850 may be arranged and positioned to sit beneath the glass forming the window 2416, which may help clean the glass and enhance the quality of the fluorescent emissions detected by the photosensor 2824. In some cases, the wiper 2850 may be coupled to a motor (shown as motor 2675 in FIG. 26). Further, the motor may or may not be controlled by a processor in the instrument assembly. The motor may also be coupled to the power structure and/or the battery of the buoy assembly.

Figure 29:
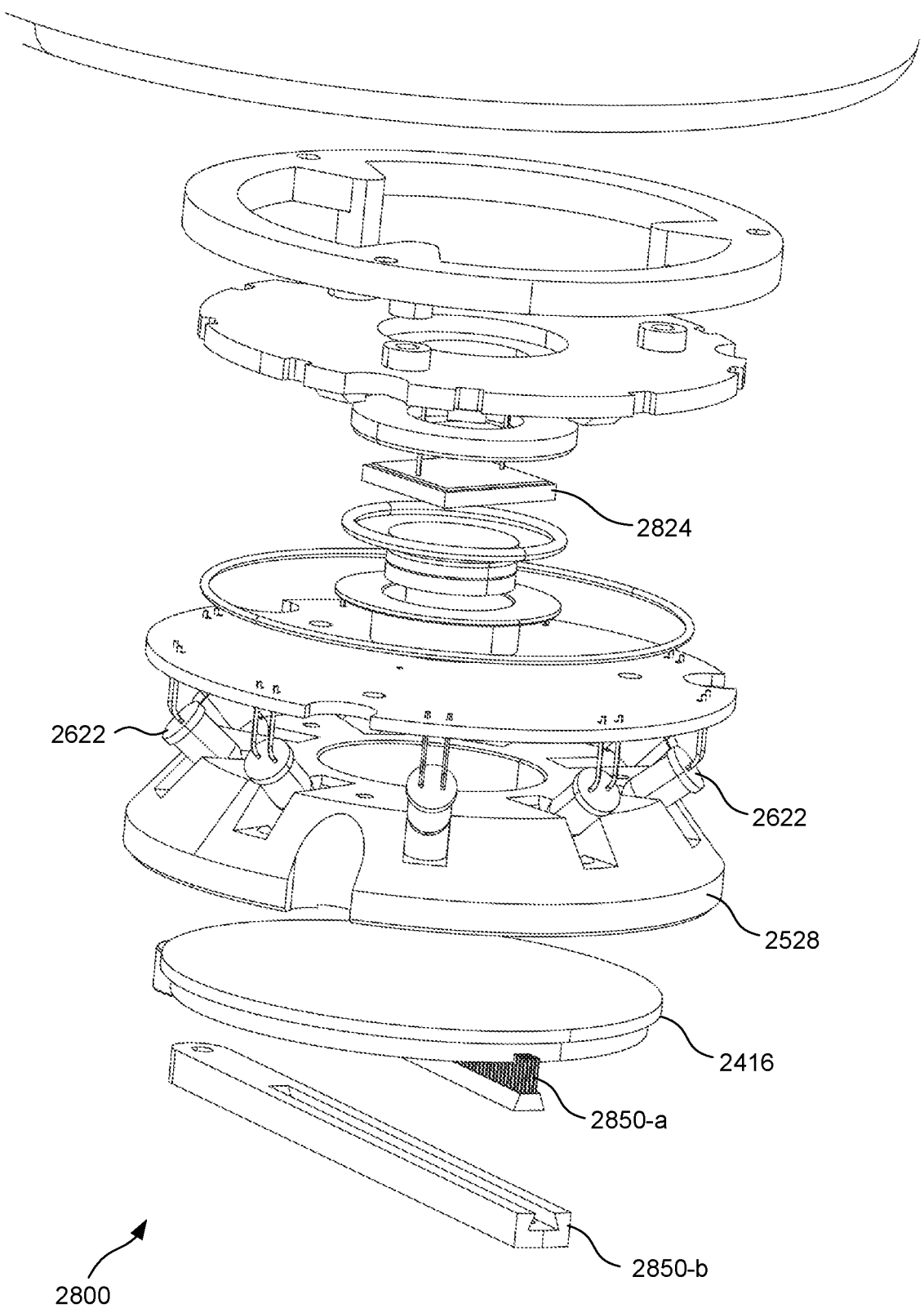
FIG. 29 shows a zoomed in view of FIG. 28, in accordance with one or more implementations.
Figure 30:
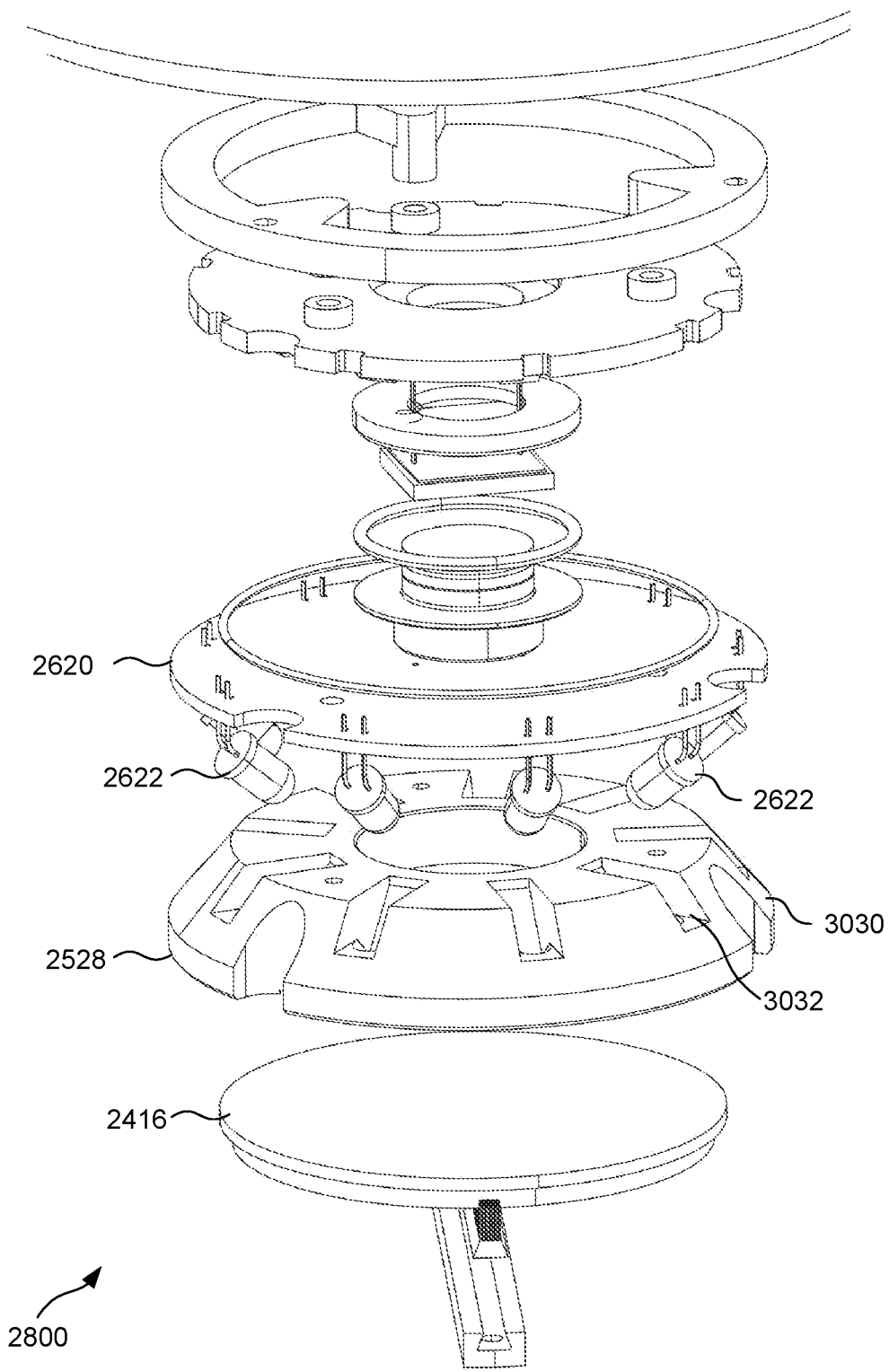
FIG. 30 shows a zoomed in view of FIG. 28, in accordance with one or more implementations.

FIGS. 29 and 30 illustrate a close up view of the instrument assembly 2800 in FIG. 28. In some examples, the instrument assemblies 2800 in FIGS. 29 and 30 may implement one or more aspects of the other instrument assemblies described throughout this application. For instance, FIG. 30 shows the prism 2528 comprising one or more angled surfaces 3030, and one or more indentations 3032 for each of the emission sources 2622. In some embodiments, these indentations 3032 may include additional angled surfaces to minimize reflections from the emission sources 2622 (e.g., by being aligned with a primary incidence angle from the emission sources 2622).

Figure 31:
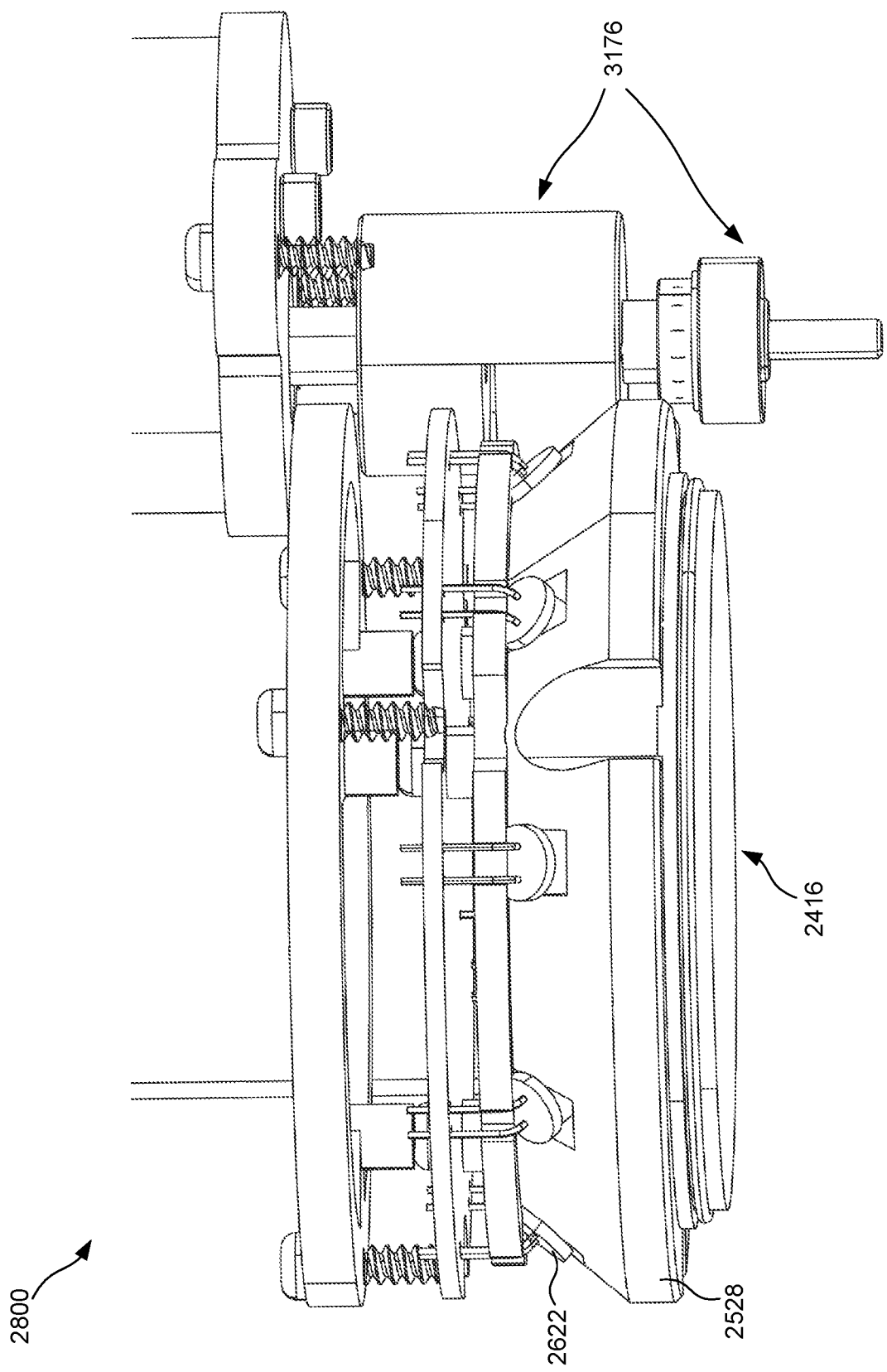
FIG. 31 illustrates a detailed front view of the prism assembly, window, and emission sources of the instrument assembly in FIG. 30, in accordance with one or more implementations.
Figure 32:
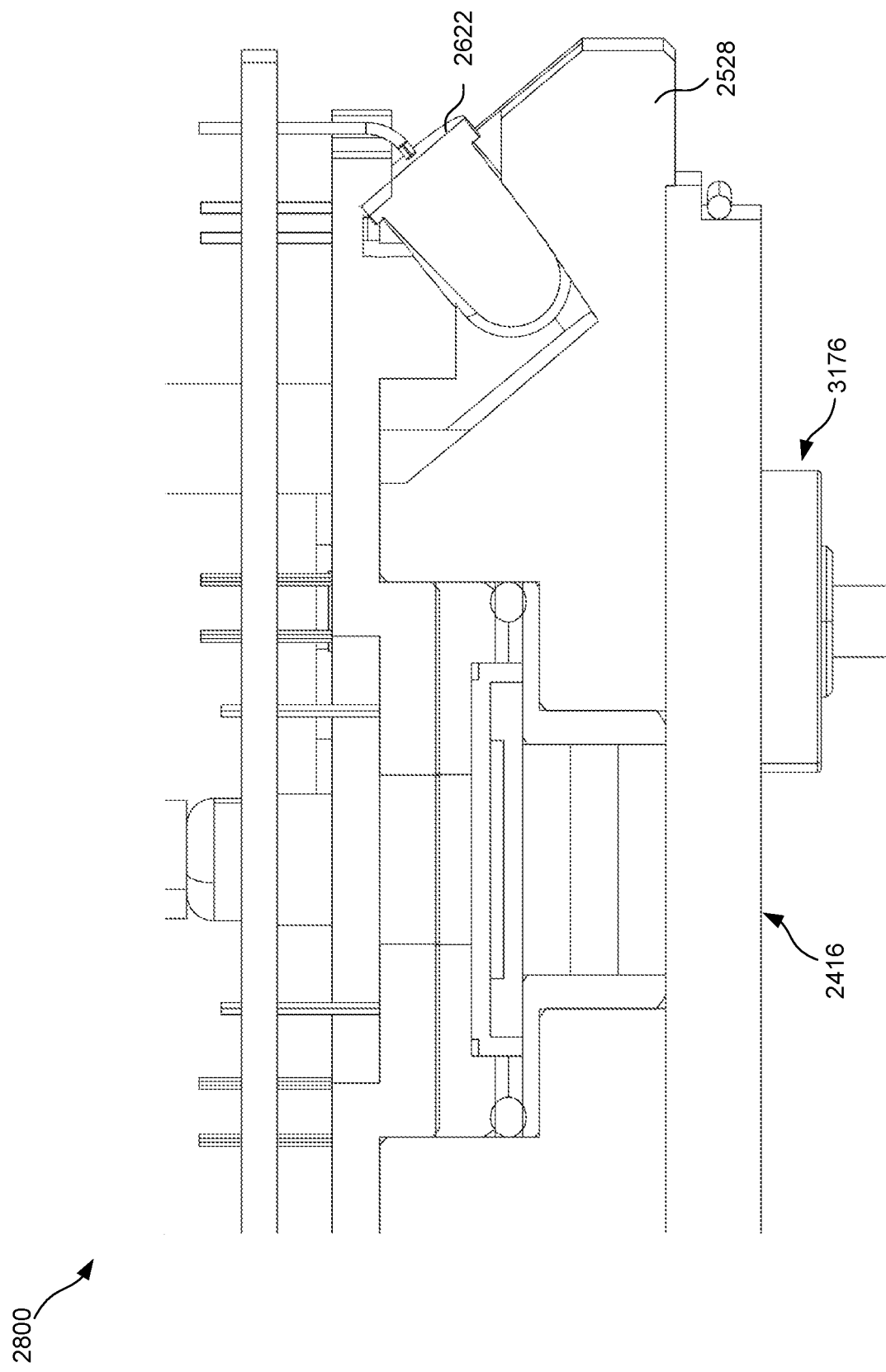
FIG. 32 shows a cross section view of FIG. 31, in accordance with one or more implementations.

FIG. 31 shows a detailed front view of the instrument assembly 2800. Specifically, FIG. 31 illustrates an actuator 3176 configured to couple the motor (shown as motor 2675 in FIG. 26) to the wiper (shown as wiper 2450 in FIG. 24). FIG. 32 illustrates a detailed cross-section view of the instrument assembly seen in FIG. 31. The actuator 3176 can include an optical assembly that indicates a rotational position of the wiper, and provides a means to reverse a direction of the motor when the wiper has passed through a desired angle of rotation (e.g., 110°. For instance, a pie-shaped opening or transparency can be formed in an opaque disc that is coupled to the motor and wiper such that rotation of the wiper causes the pie-shaped opening to correspondingly rotate. A light source can be arranged on a first side of the disc and a light reader on a second side of the disc. The motor can be controlled in a first direction while light is detected at the reader (i.e., passing through the pie-shaped opening/transparency), while the wiper rotates in a first direction. When the light is blocked by an opaque part of the disc, the motor is controlled to reverse directions. This process continues so that the wiper rotates back and forth across the window.

Figure 33:
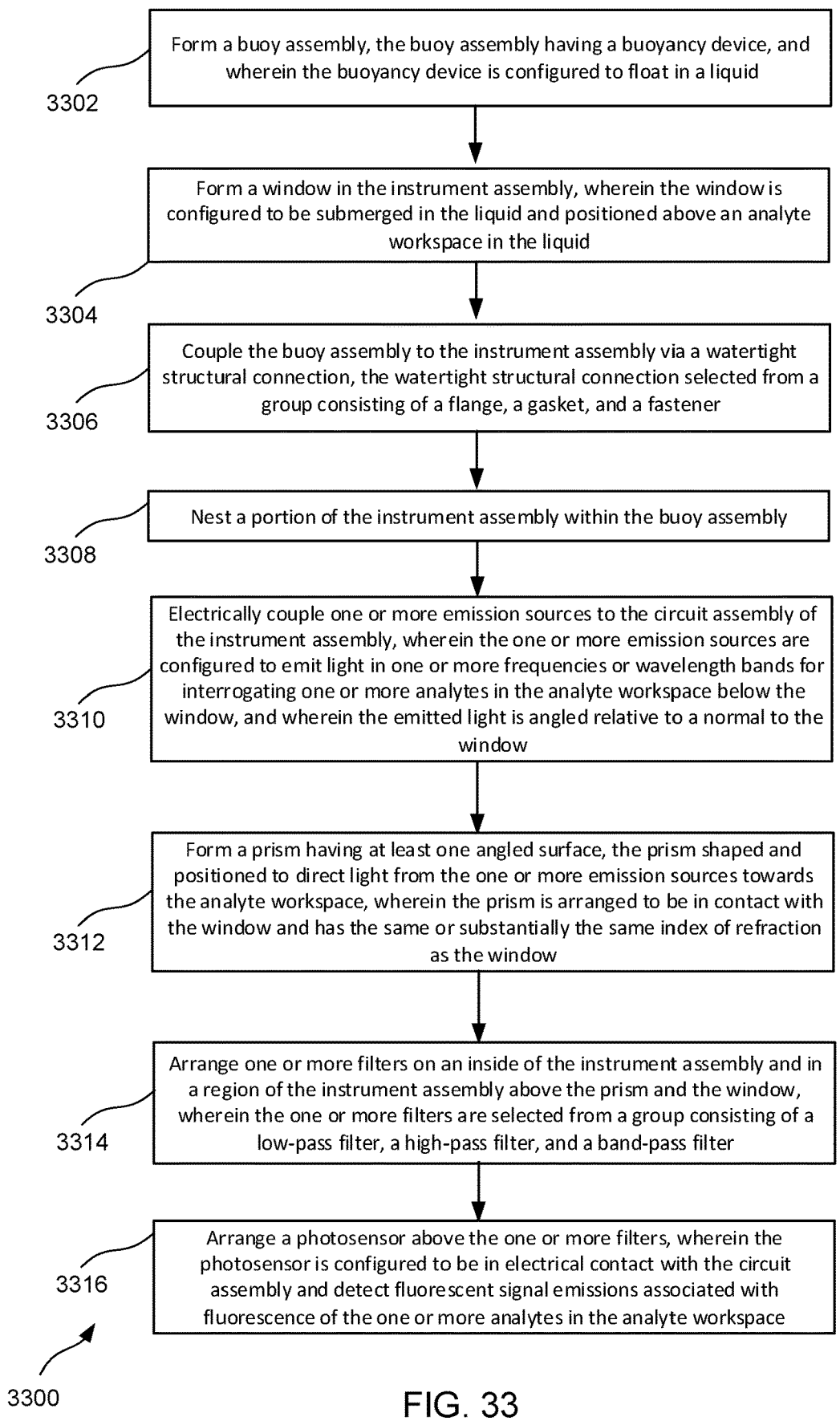
FIG. 33 illustrates a method for manufacturing a fluorometer, according to an embodiment of this disclosure.

FIG. 33 illustrates a method 3300 of an embodiment of manufacturing a fluorometer, in accordance with one or more implementations. The fluorometer may comprise an instrument assembly, a circuit assembly, a power structure, and a battery. At Block 3302, the method 3300 may comprise forming a buoy assembly, the buoy assembly having a buoyancy device, and wherein the buoyancy device is configured to float in a liquid. Further, at Block 3304, the method 3300 may comprise forming a window in the instrument assembly, wherein the window is configured to be submerged in the liquid and positioned above an analyte workspace in the liquid.

At Block 3306, the method may comprise coupling the buoy assembly to the instrument assembly via a watertight structural connection, the watertight structural connection selected from a group consisting of a flange, a gasket, and a fastener.

At Block 3308, the method may comprise nesting a portion of the instrument assembly within the buoy assembly.

At Block 3310, the method may comprise electrically coupling one or more emission sources to the circuit assembly of the instrument assembly, wherein the one or more emission sources are configured to emit light in one or more frequencies or wavelength bands for interrogating one or more analytes in the analyte workspace below the window, and wherein the emitted light is angled relative to a normal to the window.

At Block 3312, the method may comprise forming a prism having at least one angled surface, the prism shaped and positioned to direct light from the one or more emission sources towards the analyte workspace. In some embodiments, the prism is arranged to be in contact with the window. Further, the prism may be designed to have the same or substantially the same index of refraction as the window.

At Block 3314, the method may comprise arranging one or more filters on an inside of the instrument assembly and in a region of the instrument assembly above the window and optionally also above the prism or above a portion of the prism. In some embodiments, the one or more filters are selected from a group consisting of a low-pass filter, a high-pass filter, and a band-pass filter. Alternatively, at least one of the filter may be a band reject filter.

At Block 3316, the method may comprise arranging a photosensor above the one or more filters, wherein the photosensor is configured to be in electrical contact with the circuit assembly and detect fluorescent signal emissions associated with fluorescence of the one or more analytes in the analyte workspace.

Figure 34:
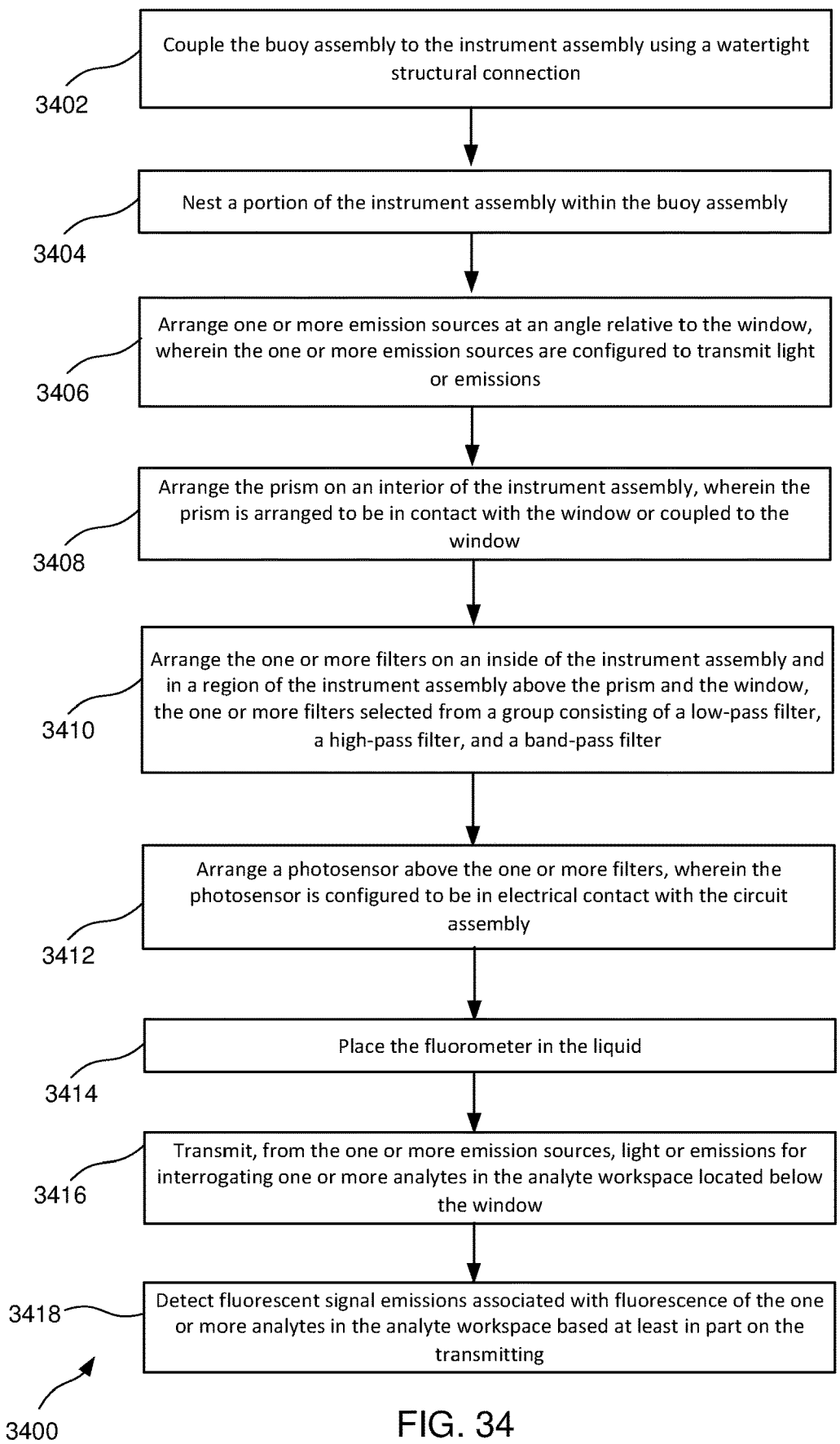
FIG. 34 illustrates a method for monitoring fluorescent peaks in an analyte workspace in a liquid using a fluorometer, according to an alternate embodiment of this disclosure.

FIG. 34 illustrates a method 3400 for monitoring fluorescent peaks in an analyte workspace in a liquid using a fluorometer, the fluorometer comprising a buoy assembly, an instrument assembly having at least a power structure, a battery, a prism, a window, one or more filters, a photosensor, and one or more emission sources. At Block 3402, the method 3400 may comprise coupling the buoy assembly to the instrument assembly using a watertight structural connection, the watertight structural connection selected from a group consisting of a flange, a gasket, and one or more fasteners. In some cases, when the fluorometer is placed in the liquid, at least a portion of the buoy assembly is configured to float above a surface of the liquid and at least a portion of the instrument assembly, including the window, is configured to be submerged below the surface of the liquid.

At Block 3404, the method 3400 may include nesting a portion of the instrument assembly within the buoy assembly.

At Block 3406, the method 3400 may include arranging one or more emission sources at an angle relative to the window, wherein the one or more emission sources are configured to transmit light or emissions.

At Block 3408, the method may include arranging the prism on an interior of the instrument assembly, wherein the prism is arranged to be in contact with the window or coupled to the window, and wherein the prism is configured to direct light from the one or more emission sources towards the analyte workspace.

At Block 3410, the method may include arranging the one or more filters on an inside of the instrument assembly and in a region of the instrument assembly above the window (and optionally above or partially above the prism), the one or more filters selected from a group consisting of a low-pass filter, a high-pass filter, and a band-pass filter.

At Block 3412, the method may include arranging a photosensor above the one or more filters, wherein the photosensor is configured to be in electrical contact with the circuit assembly.

At Block 3414, the method 3400 may include placing the fluorometer in the liquid, and at Block 3416 the method may include transmitting, from the one or more emission sources, light or emissions for interrogating one or more analytes in the analyte workspace located below the window.

At Block 3418, the method 3400 may include detecting fluorescent signal emissions associated with fluorescence of the one or more analytes in the analyte workspace based at least in part on the transmitting at Block 3416.

In some cases, the method may further comprise receiving, from the at least one photosensor, fluorescence information associated with the fluorescence emissions from the analyte workspace, the fluorescence information comprising a wavelength or frequency and a magnitude of one or more fluorescence peaks. In such cases, the method may include identifying the one or more analytes based at least in part on correlating the fluorescence information to known fluorescent signatures of algal blooms.

As used herein, the recitation of "at least one of A, B and C" is intended to mean "either A, B, C or any combination of A, B and C." The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. A fluorometer for monitoring fluorescent peaks in an analyte workspace in a liquid, comprising:
an instrument assembly, the instrument assembly comprising a circuit assembly, a casing, and a window, wherein at least a portion of the instrument assembly, including the window, is configured to be submerged within the liquid and above the analyte workspace;
a buoy assembly, wherein the buoy assembly comprises a buoyancy device and a power structure, and wherein the buoy assembly is unitary with or coupled to the instrument assembly;
one or more emission sources electrically coupled to the circuit assembly of the instrument assembly, wherein the one or more emission sources are configured to emit light in one or more frequencies or wavelength bands;
a prism arranged in contact with the window or coupled to the window via an optical fluid or adhesive, wherein the prism is configured to direct emissions from the one or more emission sources towards the analyte workspace, the prism including at least one angled surface facing the one or more emission sources;
at least one photosensor positioned above the window and configured to detect fluorescence emissions of one or more analytes being interrogated in the analyte workspace; and
a filter array comprising one or more filters and positioned between the window and the photosensor, the one or more filters selected from a group consisting of a low-pass filter, a high-pass filter, and a band-pass filter;
a filter housing comprising a reflective inner surface and arranged within a region of the instrument assembly between the prism and the photosensor, and wherein the filter housing is shaped and sized to receive the filter assembly.

2. A fluorometer for monitoring fluorescent peaks in an analyte workspace in a liquid, comprising:
an instrument assembly, the instrument assembly comprising a circuit assembly, a casing, and a window, wherein at least a portion of the instrument assembly, including the window, is configured to be submerged within the liquid and above the analyte workspace;
a buoy assembly, wherein the buoy assembly comprises a buoyancy device and a power structure, and wherein the buoy assembly is unitary with or coupled to the instrument assembly;
one or more emission sources electrically coupled to the circuit assembly of the instrument assembly, wherein the one or more emission sources are configured to emit light in one or more frequencies or wavelength bands;
a prism arranged in contact with the window or coupled to the window via an optical fluid or adhesive, wherein the prism is configured to direct emissions from the one or more emission sources towards the analyte workspace, the prism including at least one angled surface facing the one or more emission sources;
at least one photosensor positioned above the window and configured to detect fluorescence emissions of one or more analytes being interrogated in the analyte workspace; and
a filter array comprising one or more filters and positioned between the window and the photosensor, the one or more filters selected from a group consisting of a low-pass filter, a high-pass filter, and a band-pass filter;
wherein the prism further comprises an annular aperture having a reflective inner surface.

3. A fluorometer for monitoring fluorescent peaks in an analyte workspace in a liquid, comprising:
an instrument assembly, the instrument assembly comprising a circuit assembly, a casing, and a window, wherein at least a portion of the instrument assembly, including the window, is configured to be submerged within the liquid and above the analyte workspace;

a buoy assembly, wherein the buoy assembly comprises a buoyancy device and a power structure, and wherein the buoy assembly is unitary with or coupled to the instrument assembly;

one or more emission sources electrically coupled to the circuit assembly of the instrument assembly, wherein the one or more emission sources are configured to emit light in one or more frequencies or wavelength bands;

a prism arranged in contact with the window or coupled to the window via an optical fluid or adhesive, wherein the prism is configured to direct emissions from the one or more emission sources towards the analyte workspace, the prism including at least one angled surface facing the one or more emission sources;

at least one photosensor positioned above the window and configured to detect fluorescence emissions of one or more analytes being interrogated in the analyte workspace; and a filter array comprising one or more filters and positioned between the window and the photosensor, the one or more filters selected from a group consisting of a low-pass filter, a high-pass filter, and a band-pass filter;

wherein the prism comprises an indentation shaped and sized to receive at least a portion of the window.

4. A fluorometer for monitoring fluorescent peaks in an analyte workspace in a liquid, comprising:

an instrument assembly, the instrument assembly comprising a circuit assembly, a casing, and a window, wherein at least a portion of the instrument assembly, including the window, is configured to be submerged within the liquid and above the analyte workspace;

a buoy assembly, wherein the buoy assembly comprises a buoyancy device and a power structure, and wherein the buoy assembly is unitary with or coupled to the instrument assembly:

one or more emission sources electrically coupled to the circuit assembly of the instrument assembly, wherein the one or more emission sources are configured to emit light in one or more frequencies or wavelength bands;

a prism arranged in contact with the window or coupled to the window via an optical fluid or adhesive, wherein the prism is configured to direct emissions from the one or more emission sources towards the analyte workspace, the prism including at least one angled surface facing the one or more emission sources;

at least one photosensor positioned above the window and configured to detect fluorescence emissions of one or more analytes being interrogated in the analyte workspace; and a filter array comprising one or more filters and positioned between the window and the photosensor, the one or more filters selected from a group consisting of a low-pass filter, a high-pass filter, and a band-pass filter;

wherein the prism further comprises an annular aperture having a reflective coating on its inside edge.

5. A fluorometer for monitoring fluorescent peaks in an analyte workspace in a liquid, comprising:

an instrument assembly, the instrument assembly comprising a circuit assembly, a casing, and a window, wherein at least a portion of the instrument assembly, including the window, is configured to be submerged within the liquid and above the analyte workspace;

a buoy assembly, wherein the buoy assembly comprises a buoyancy device and a power structure, and wherein the buoy assembly is unitary with or coupled to the instrument assembly;

one or more emission sources electrically coupled to the circuit assembly of the instrument assembly, wherein the one or more emission sources are configured to emit light in one or more frequencies or wavelength bands;

a prism arranged in contact with the window or coupled to the window via an optical fluid or adhesive, wherein the prism is configured to direct emissions from the one or more emission sources towards the analyte workspace, the prism including at least one angled surface facing the one or more emission sources;

at least one photosensor positioned above the window and configured to detect fluorescence emissions of one or more analytes being interrogated in the analyte workspace; and a filter array comprising one or more filters and positioned between the window and the photosensor, the one or more filters selected from a group consisting of a low-pass filter, a high-pass filter, and a band-pass filter;

wherein a bottom of the window is coated with one or more anti-reflection layers.

6. A fluorometer for monitoring fluorescent peaks in an analyte workspace in a liquid, comprising:

an instrument assembly, the instrument assembly comprising a circuit assembly, a casing, and a window, wherein at least a portion of the instrument assembly, including the window, is configured to be submerged within the liquid and above the analyte workspace;

a buoy assembly, wherein the buoy assembly comprises a buoyancy device and a power structure, and wherein the buoy assembly is unitary with or coupled to the instrument assembly;

one or more emission sources electrically coupled to the circuit assembly of the instrument assembly, wherein the one or more emission sources are configured to emit light in one or more frequencies or wavelength bands;

a prism arranged in contact with the window or coupled to the window via an optical fluid or adhesive, wherein the prism is configured to direct emissions from the one or more emission sources towards the analyte workspace, the prism including at least one angled surface facing the one or more emission sources;

at least one photosensor positioned above the window and configured to detect fluorescence emissions of one or more analytes being interrogated in the analyte workspace; and a filter array comprising one or more filters and positioned between the window and the photosensor, the one or more filters selected from a group consisting of a low-pass filter, a high-pass filter, and a band-pass filter;

wherein the at least one angled surface comprises an anti-reflection coating, and wherein at least one emission source is angled relative to a normal to the at least one angled surface.

7. The fluorometer of claim 6, further comprising:

a reflective coating or surface on an inside of the casing; and wherein a respective line perpendicular to each of the one or more emission sources is one of: angled inward toward a central axis of the instrument assembly; or angled outward such that the emissions reflect off the reflective coating or surface on the inside of the casing.

8. The fluorometer of claim 7, wherein a distance between a center of the analyte workspace and the bottom of the window is based at least in part on an angle of incidence of emissions from the one or more emission sources with an angled surface of the prism, and wherein the distance is lower when the emissions intersect the angled surface at an angle relative to a normal to the angled surface as compared to when the emissions are perpendicular to the angled surface.

* * * * *